(12) United States Patent
Atkins et al.

(10) Patent No.: US 11,565,057 B2
(45) Date of Patent: Jan. 31, 2023

(54) CALIBRATED DOSE CONTROL

(71) Applicant: JUUL Labs, Inc., San Francisco, CA (US)

(72) Inventors: Ariel Atkins, San Francisco, CA (US); Adam Bowen, San Mateo, CA (US); Bradley J. Ingebrethsen, Saugerties, NY (US); Esteban Leon Duque, San Francisco, CA (US); James Monsees, San Francisco, CA (US)

(73) Assignee: JUUL Labs, Inc., San Francisco, CA (US)

( * ) Notice: Subject to any disclaimer, the term of this patent is extended or adjusted under 35 U.S.C. 154(b) by 442 days.

(21) Appl. No.: 16/719,884

(22) Filed: Dec. 18, 2019

(65) Prior Publication Data

US 2020/0120987 A1 Apr. 23, 2020

Related U.S. Application Data

(63) Continuation of application No. 14/960,259, filed on Dec. 4, 2015, now Pat. No. 10,512,282.

(Continued)

(51) Int. Cl.
*A61M 11/04* (2006.01)
*A24F 40/53* (2020.01)
(Continued)

(52) U.S. Cl.
CPC ......... *A61M 11/042* (2014.02); *A24B 15/167* (2016.11); *A24F 40/50* (2020.01); *A24F 40/53* (2020.01); *A24F 40/57* (2020.01); *A61M 15/0065* (2013.01); *A61M 15/06* (2013.01);

*G01K 7/22* (2013.01); *G01N 33/0027* (2013.01); *H05B 1/0244* (2013.01); *A24F 40/10* (2020.01);
(Continued)

(58) Field of Classification Search
CPC ............ A61M 11/042; A61M 15/0065; A61M 15/06; A24F 40/10; A24F 40/50; A24F 40/51; A24F 40/57; A24F 40/65
See application file for complete search history.

(56) References Cited

U.S. PATENT DOCUMENTS

| 4,941,483 A | 7/1990 | Ridings et al. |
| 4,947,874 A | 8/1990 | Brooks et al. |

(Continued)

FOREIGN PATENT DOCUMENTS

| CN | 1491525 A | 4/2004 |
| CN | 103501847 A | 1/2014 |

(Continued)

*Primary Examiner* — Joseph D. Boecker
(74) *Attorney, Agent, or Firm* — Mintz Levin Cohn Ferris Glovsky and Popeo, P.C.

(57) ABSTRACT

Methods and vaporizer apparatuses that estimate, measure and/or predict the amount of vapor and/or material (including active ingredients) released by the vaporizer apparatus. In particular, described herein are electronic vaporizers and methods of using them that determine a dose/amount of vapor and/or a material in the vapor based primarily or exclusively on the electrical and thermal properties, e.g., power or energy applied to the vaporizing element (e.g., heating coil) and the temperature of the material immediately before and as it is vaporized. Dose information may be used to control operation of the device and/or reported to the user.

46 Claims, 11 Drawing Sheets

Related U.S. Application Data

(60) Provisional application No. 62/199,828, filed on Jul. 31, 2015, provisional application No. 62/088,464, filed on Dec. 5, 2014.

(51) Int. Cl.
*A24F 40/50* (2020.01)
*A24F 40/57* (2020.01)
*A61M 15/00* (2006.01)
*A61M 15/06* (2006.01)
*A24F 40/10* (2020.01)
*A24F 40/51* (2020.01)
*A24B 15/167* (2020.01)
*G01K 7/22* (2006.01)
*G01N 33/00* (2006.01)
*H05B 1/02* (2006.01)
*A61M 16/00* (2006.01)
*A24F 40/65* (2020.01)

(52) U.S. Cl.
CPC .............. *A24F 40/51* (2020.01); *A24F 40/65* (2020.01); *A61M 2016/0027* (2013.01); *A61M 2016/0039* (2013.01); *A61M 2205/14* (2013.01); *A61M 2205/33* (2013.01); *A61M 2205/3368* (2013.01); *A61M 2205/581* (2013.01); *A61M 2205/582* (2013.01); *A61M 2205/583* (2013.01); *A61M 2205/8206* (2013.01); *A61M 2205/8237* (2013.01)

(56) References Cited

U.S. PATENT DOCUMENTS

| | | | |
|---|---|---|---|
| 4,947,875 | A | 8/1990 | Brooks et al. |
| 5,175,791 | A | 12/1992 | Muderlak et al. |
| 6,095,153 | A | 8/2000 | Kessler et al. |
| 6,443,146 | B1 | 9/2002 | Voges |
| 6,501,052 | B2 | 12/2002 | Cox et al. |
| 6,701,922 | B2 | 3/2004 | Hindle et al. |
| 6,909,840 | B2 | 6/2005 | Harwig et al. |
| 7,143,766 | B2 | 12/2006 | Schuster et al. |
| 7,173,222 | B2 | 2/2007 | Cox et al. |
| 8,387,612 | B2 | 3/2013 | Damani et al. |
| 8,485,180 | B2 | 7/2013 | Smutney et al. |
| 8,550,069 | B2 | 10/2013 | Alelov |
| 8,714,150 | B2 | 5/2014 | Alelov |
| 8,851,068 | B2 | 10/2014 | Cohen et al. |
| 8,881,737 | B2 | 11/2014 | Collett et al. |
| 8,910,630 | B2 | 12/2014 | Todd |
| 8,910,640 | B2 | 12/2014 | Sears et al. |
| 8,961,492 | B2 | 2/2015 | Imran et al. |
| 9,078,473 | B2 | 7/2015 | Worm et al. |
| 9,095,174 | B2 | 8/2015 | Capuano |
| 9,247,773 | B2 | 2/2016 | Memari et al. |
| 9,414,629 | B2 | 8/2016 | Egoyants et al. |
| 9,423,152 | B2 | 8/2016 | Ampolini et al. |
| 9,427,022 | B2 | 8/2016 | Levin et al. |
| 9,549,573 | B2 | 1/2017 | Monsees et al. |
| 9,668,522 | B2 | 6/2017 | Memari et al. |
| 9,682,203 | B2 | 6/2017 | Dahne et al. |
| 9,743,691 | B2 | 8/2017 | Minskoff et al. |
| 9,802,011 | B2 | 10/2017 | Davidson et al. |
| 9,974,743 | B2 | 5/2018 | Rose et al. |
| 10,039,323 | B2 | 8/2018 | Schuler et al. |
| 10,058,124 | B2 | 8/2018 | Monsees et al. |
| 10,512,282 | B2 | 12/2019 | Bowen et al. |
| 2003/0132219 | A1* | 7/2003 | Cox ................ A61M 15/025 392/397 |
| 2005/0034723 | A1 | 2/2005 | Bennett et al. |
| 2005/0268911 | A1 | 12/2005 | Cross et al. |
| 2008/0038363 | A1 | 2/2008 | Zaffaroni et al. |
| 2008/0241255 | A1 | 10/2008 | Rose et al. |
| 2008/0257367 | A1 | 10/2008 | Paterno et al. |
| 2010/0181387 | A1 | 7/2010 | Zaffaroni et al. |
| 2011/0265806 | A1 | 11/2011 | Alarcon et al. |
| 2011/0284520 | A1 | 11/2011 | Fong |
| 2012/0048266 | A1* | 3/2012 | Alelov ............ A61M 15/0003 128/203.14 |
| 2013/0023850 | A1 | 1/2013 | Imran et al. |
| 2013/0199528 | A1 | 8/2013 | Goodman et al. |
| 2013/0255702 | A1 | 10/2013 | Griffith, Jr. et al. |
| 2014/0041658 | A1 | 2/2014 | Goodman et al. |
| 2014/0096781 | A1 | 4/2014 | Sears et al. |
| 2014/0096782 | A1 | 4/2014 | Ampolini et al. |
| 2014/0123990 | A1 | 5/2014 | Timmermans |
| 2014/0144429 | A1* | 5/2014 | Wensley ............ A61M 15/06 128/200.14 |
| 2014/0261486 | A1 | 9/2014 | Potter et al. |
| 2014/0270727 | A1 | 9/2014 | Ampolini et al. |
| 2014/0338680 | A1 | 11/2014 | Abramov et al. |
| 2014/0345635 | A1 | 11/2014 | Rabinowitz et al. |
| 2015/0040925 | A1 | 2/2015 | Saleem et al. |
| 2015/0047661 | A1 | 2/2015 | Blackley et al. |
| 2015/0208729 | A1 | 7/2015 | Monsees et al. |
| 2015/0223520 | A1 | 8/2015 | Phillips et al. |
| 2015/0223523 | A1 | 8/2015 | McCullough |
| 2015/0245654 | A1 | 9/2015 | Memari et al. |
| 2015/0245655 | A1 | 9/2015 | Memari et al. |
| 2015/0245657 | A1 | 9/2015 | Memari et al. |
| 2015/0245665 | A1 | 9/2015 | Memari et al. |
| 2015/0245666 | A1 | 9/2015 | Memari et al. |
| 2015/0245667 | A1 | 9/2015 | Memari et al. |
| 2015/0245668 | A1 | 9/2015 | Memari et al. |
| 2015/0272220 | A1* | 10/2015 | Spinka ................. A24F 40/60 131/329 |
| 2015/0320116 | A1 | 11/2015 | Bleloch et al. |
| 2016/0018347 | A1 | 1/2016 | Drbal et al. |
| 2016/0044963 | A1 | 2/2016 | Saleem |
| 2016/0095355 | A1 | 4/2016 | Hearn |
| 2016/0150824 | A1 | 6/2016 | Memari et al. |
| 2016/0166564 | A1 | 6/2016 | Myers et al. |
| 2016/0219938 | A1 | 8/2016 | Mamoun et al. |
| 2016/0255878 | A1 | 9/2016 | Huang et al. |
| 2016/0295922 | A1 | 10/2016 | John et al. |
| 2016/0360785 | A1 | 12/2016 | Bless et al. |
| 2017/0014582 | A1* | 1/2017 | Skoda ............ A61M 15/0021 |
| 2017/0027232 | A1 | 2/2017 | Scheck et al. |
| 2017/0030882 | A1 | 2/2017 | Skoda |
| 2017/0086502 | A1 | 3/2017 | Hearn et al. |
| 2017/0094999 | A1 | 4/2017 | Hearn et al. |
| 2017/0105449 | A1 | 4/2017 | Hearn et al. |
| 2017/0146005 | A1 | 5/2017 | Edelen |
| 2017/0251726 | A1 | 9/2017 | Nielsen |
| 2017/0251727 | A1 | 9/2017 | Nielsen |
| 2018/0117268 | A1 | 5/2018 | Selby et al. |
| 2018/0141073 | A1 | 5/2018 | Tan et al. |
| 2018/0162769 | A1 | 6/2018 | Peuchert et al. |
| 2018/0168226 | A1 | 6/2018 | Mironov et al. |
| 2018/0303169 | A1 | 10/2018 | Sears et al. |

FOREIGN PATENT DOCUMENTS

| | | |
|---|---|---|
| CN | 103997921 B | 4/2017 |
| CN | 103948170 B | 11/2018 |
| EP | 0358114 A2 | 3/1990 |
| EP | 0503767 A1 | 9/1992 |
| EP | 0532194 A1 | 3/1993 |
| EP | 2468116 A1 | 6/2012 |
| EP | 2468117 A1 | 6/2012 |
| EP | 2982255 B1 | 5/2019 |
| JP | 2014501107 A | 1/2014 |
| JP | 2015507477 A | 3/2015 |
| KR | 101613742 B1 | 4/2016 |
| WO | WO-2011137453 A2 | 11/2011 |
| WO | WO-2012027350 A2 | 3/2012 |
| WO | WO-2012/085207 A1 | 6/2012 |
| WO | WO-2013034453 A1 | 3/2013 |
| WO | WO-2013/098398 A2 | 7/2013 |
| WO | WO-2013131763 A1 | 9/2013 |
| WO | WO-2014127446 A1 | 8/2014 |
| WO | WO-2015/124878 A1 | 8/2015 |
| WO | WO-2015/148547 A1 | 10/2015 |

(56) References Cited

FOREIGN PATENT DOCUMENTS

| | | |
|---|---|---|
| WO | WO-2016050246 A1 | 4/2016 |
| WO | WO-2016050247 A1 | 4/2016 |
| WO | WO-2017029268 A1 | 2/2017 |
| WO | WO-2017029270 A1 | 2/2017 |
| WO | WO-2017046593 A2 | 3/2017 |
| WO | WO-2017084107 A1 | 5/2017 |

* cited by examiner

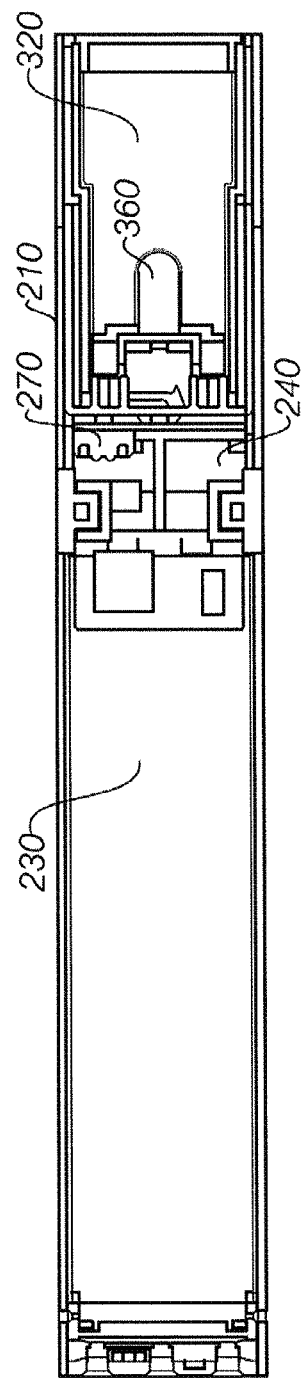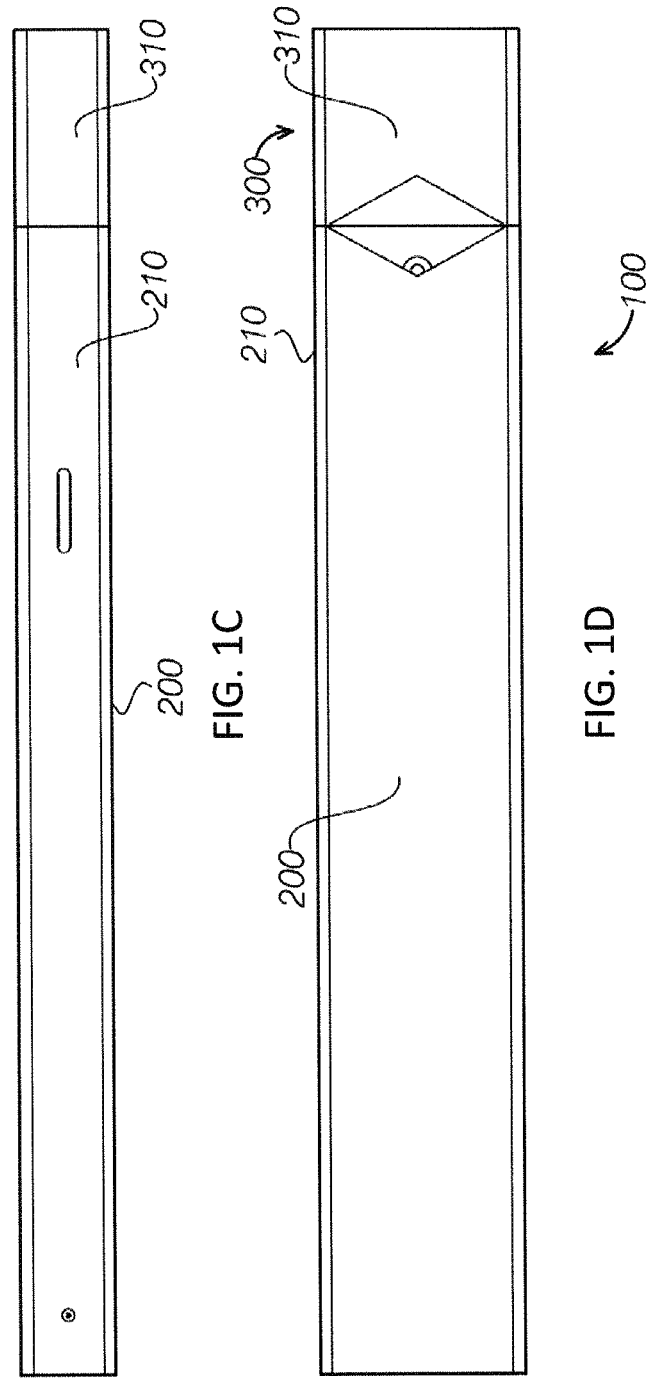
FIG. 1B
FIG. 1C
FIG. 1D

| MEASURED TPM (mg) | PREDICTED TPM (mg) | % ERROR |
|---|---|---|
| 37.0 | 34.99 | -5.4% |
| 34.5 | 34.39 | -0.3% |
| 33.0 | 38.42 | 16.4% |
| 33.6 | 35.96 | 7.0% |
| 35.2 | 39.45 | 12.1% |
| 36.3 | 39.39 | 8.5% |
| 36.5 | 39.39 | 7.9% |
| 45.5 | 47.85 | 5.2% |
| 38.4 | 36.14 | -5.9% |
| 43.7 | 42.06 | -3.8% |
| 34.4 | 33.79 | -1.8% |
| 43.2 | 40.85 | -5.4% |
| 38.2 | 37.66 | -1.4% |
| 40.8 | 39.64 | -2.8% |
| 40.5 | 42.05 | 3.8% |
| 45.2 | 43.75 | -3.2% |
| 46.8 | 44.75 | -4.4% |
| 41.5 | 35.22 | -15.1% |
| 48.8 | 43.51 | -10.8% |
| 49.6 | 45.66 | -7.9% |
| 51.3 | 50.08 | -2.4% |
| 32.8 | 36.70 | 11.9% |
| 43.8 | 47.58 | 8.6% |
| 37.0 | 40.72 | 10.1% |
| 39.8 | 42.17 | 6.0% |
| 40.9 | 43.12 | 5.4% |
| 44.7 | 44.30 | -0.9% |
| 42.5 | 42.57 | 0.2% |
| 56.5 | 55.78 | -1.3% |
| 47.2 | 46.22 | -2.1% |
| 35.9 | 35.47 | -1.2% |

FIG. 3

| TARGET (mg) | 40.00 |
|---|---|
| MEAN (mg) | 42.13 |
| STANDARD DEVIATION | 2.51 |
| CV | 5.96% |
| MAX ERROR FROM TARGET | 16.50% |
| MAX ERROR FROM MEAN | 10.62% |

| MEASURED TPM (mg) | % ERROR FROM TARGET | % ERROR FROM MEAN |
|---|---|---|
| 38.6 | -3.50% | -8.37% |
| 38.5 | -3.75% | -8.61% |
| 40.2 | 0.50% | -4.58% |
| 41.8 | 4.50% | -0.78% |
| 45.5 | 13.75% | 8.00% |
| 44.1 | 10.25% | 4.68% |
| 45.8 | 14.50% | 8.72% |
| 44.2 | 10.50% | 4.92% |
| 41.6 | 4.00% | -1.25% |
| 38.2 | -4.50% | -9.32% |
| 46.5 | 16.25% | 10.38% |
| 42.8 | 7.00% | 1.60% |
| 40.5 | 1.25% | -3.86% |
| 43.5 | 8.75% | 3.26% |
| 40.5 | 1.25% | -3.86% |
| 42.6 | 6.50% | 1.12% |
| 40.4 | 1.00% | -4.10% |
| 43.9 | 9.75% | 4.21% |
| 38.6 | -3.50% | -8.37% |
| 42.8 | 7.00% | 1.60% |
| 41.0 | 2.50% | -2.68% |
| 46.6 | 16.50% | 10.62% |
| 43.4 | 8.50% | 3.02% |
| 40.3 | 0.75% | -4.34% |
| 41.3 | 3.25% | -1.97% |

| DURATION (seconds) | TPM (mg) |
|---|---|
| 0.1 | 0.07 |
| 0.3 | 0.12 |
| 0.5 | 0.20 |
| 0.7 | 0.28 |
| 1.0 | 0.33 |
| 1.5 | 0.70 |
| 2.0 | 0.95 |
| 2.5 | 1.51 |
| 3.0 | 2.10 |
| ... | ... |

CALIBRATED DOSE CONTROL

CROSS REFERENCE TO RELATED APPLICATIONS

This application is a continuation of U.S. Nonprovisional patent application Ser. No. 14/960,259 filed Dec. 4, 2015, titled "CALIBRATED DOSE CONTROL," which claims priority to U.S. Provisional Application No. 62/088,464 filed Dec. 5, 2014, titled "CALIBRATED DOSE CONTROL AND HEAT BLOCK RESERVOIR FOR E-VAPORIZER DEVICE," and U.S. Provisional Application No. 62/199,828, filed Jul. 31, 2015, titled "CALIBRATED DOSE CONTROL," each of which is herein incorporated by reference in its entirety.

This patent application may also be related to U.S. patent application Ser. No. 14/581,666, filed Dec. 23, 2014 and titled "VAPORIZATION DEVICE SYSTEMS AND METHODS," Publication No. US-2015-0208729-A1 which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, systems and methods described herein may be useful for determining a dosage of a vapor and/or an amount of active ingredient in the vapor to a user inhaling the vapor.

BACKGROUND

Vaporizing devices, including electronic vaporizer devices or e-vaporizer devices, allow the delivery of vapor containing one or more active ingredient by inhalation of the vapor. Electronic vaporizer devices are gaining increasing popularity both for prescriptive medical use, in delivering medicaments, and for consumption of tobacco and other plant-based smokeable materials. Electronic vaporizer devices in particular may be portable, self-contained and convenient for use. Unfortunately, such devices, even when adapted for medical use, may vary in the amount of vapor and/or active ingredient provided.

To date, attempts to determine the dosage of vapor and/or an active ingredient in the vapor have been unsatisfactory. Systems that pre-determine dosage by restricting the amount of material to be delivered in a session assume, often incorrectly, that all of the material will be inhaled, and may not be adjustable for partial dosages. Such systems may also meter the amount of material, and require accurate measurement of the mass and/or volume of material being delivered for vaporization, or measure the difference between a starting mass/volume and post-delivery mass or volume. These measurements may be difficult, requiring a high level of accuracy and expense, and may result in inaccurate results.

What is needed is a method and apparatus (e.g., system and/or device) for delivering vapor and accurately, e.g., within a reasonable margin of accuracy/error, the delivered dosage. In particular, it would be helpful to provide methods and apparatuses for determining delivered doses of vapor and/or ingredients within the vapor by monitoring the electrical activity, and in some cases the temperature (which may be estimated electrically or measured directly) of the apparatus. Further, it would be helpful to provide such methods and apparatuses to deliver predetermined doses and/or to alert a use or caregiver when a threshold dosage has been reached or exceeded. Further, it may also be helpful to provide an electronic record of doses delivered.

SUMMARY OF THE DISCLOSURE

Disclosed herein are methods and apparatuses, including devices and systems that may estimate, measure and/or predict the amount of vapor and/or material (including active ingredients) in the vapor that can be delivered to a user. In particular, described herein are electronic vaporizers and methods of using them that determined a dose/amount of vapor and/or a material in the vapor based primarily or exclusively on the electrical properties, e.g., power or energy applied to the vaporizing element (e.g., coil) and, in some variations, the temperature of the material as it is vaporized. In some variations the temperature of the material as it is being vaporized may be estimated/approximated based on the electrical properties, e.g., the temperature coefficient of resistance or TCR, of the vaporizing element.

In general, the methods and apparatuses described herein may accurately determine the dosage delivered to within about 20% of an actual dosage delivered (e.g., within about 19%, within about 18%, within about 17%, within about 16%, within about 15%, within about 14%, within about 13%, within about 12%, within about 11%, within about 10%, etc.).

Also described herein are method and apparatuses for calibrating. Calibration may be performed automatically or manually, and may be performed at the factory. In some variations, calibration may be performed by the user. Calibration may include the input of values, including constant values. Calibration may be performed when the material being vaporized, including either or both the carrier and/or the active ingredient, are changed.

Although many of the examples described herein are directed to determining dosage of nicotine or other tobacco-related materials, it should be understood that these methods and apparatuses may be used for delivery and dosage determination of any vaporizable material, including therapeutic drugs. Examples of active ingredients that may be used as described herein are provided below, and may include botanicals, nutraceuticals, pharmaceuticals, and the like, including combinations of these. The methods and apparatuses described herein may provide relatively pure material directly to the lungs, which may speed the action in the body, including both the time of onset and the off-time.

In some embodiments, disclosed herein are methods and devices that allow a user to control the amount of vapor generated from a vaporizable material. This allows for customization of the vaping experience for a variety of vaporizable materials, and an overall improved user experience. The methods of this disclosure can be implemented using any electronic vaporizer device or vaporizing device configured as specified herein.

For example, the present disclosure provides a method of dose control and calibration of electronic vaporizer devices comprising measuring the amount of material vaporized from a vaporizable material from an electronic vaporizer device or vaporizing device relative to power, time and temperature. These methods and apparatuses may include a vaporized dose (e.g. mass) prediction system comprising setting-up a relationship of total particulate matter (TPM) or active ingredient vaporization or release as a function of temperature (which may be determined by electrical resistivity or otherwise measured by a temperature-proportionate property), time (which may be associated with detection of puffing/inhalation by the user) and power consumption of the vaporizing element(s). In some embodiments, the present disclosure provides a method of metered dose control and calibration of electronic vaporizer devices comprising measuring the amount of material vaporized from a vaporizable material from an electronic vaporizer device or vaporizing device relative to power and temperature; particularly, a method comprising a vaporized dose prediction system comprising setting-up a relationship of total particulate matter (TPM) or active ingredient vaporization or release as a function of temperature and power consumption.

Thus, described herein are methods of determining a dose of a vaporizable material delivered to a user of a vaporizing device over a time period. The time period typically comprises a plurality of sequential time intervals. In any of these methods and apparatuses the vaporizing device may include a heater controller, a heater, a source of the vaporizable material and a vaporized dose predictor unit. For example, a method may include: calculating, for each of the sequential time intervals, a partial dose, wherein the partial dose is calculated from a power delivered by the heater controller to the heater to vaporize the vaporizable material during a partial dose time interval, a temperature of the vaporizable material being vaporized during the partial dose time interval, and a temperature of the vaporizable material being vaporized before the partial dose time interval; and summing the calculated partial doses in the vaporized dose predictor unit to determine a total dose of vapor delivered during the time period.

Any of the calculation or summing steps may be performed in the device (e.g., locally, e.g., within a controller which may include or be part of the vaporized dose predictor unit that is within the same housing as other portions of the device such as the heater control), and/or they may be performed remotely, e.g., in a processor that receives, such as wirelessly, the power, temperature(s) and/or partial dose information. The vaporized dose predictor unit (which may be referred to herein as a vaporized dose predictor or vaporized dose predictor circuitry, or vaporized dose predictor control logic) may be located remotely from other portions of the device, including in a remote server (e.g., cloud-based server, smartphone or wearable apparatus, etc.) and may receive the information wirelessly.

In general, any of these methods may also include determining an amount of active ingredient delivered to the user based on the total dose of vapor delivered. This may be performed using the concentration of active material within the source of vaporizable material, for example (e.g., giving the amount of active ingredient/unit mass or unit volume or the vaporizable material in the source of vaporizable material).

Any of these methods may also include determining a change in temperature ($\Delta T$) of the vaporizable material being vaporized for each of the sequential time intervals relative the temperature of the vaporizable material being vaporized.

Any appropriate time interval (dose time interval), which may be sequential (e.g., sequential time intervals) may be used, and may be based on or reflective of the sampling rate of the apparatus for determining the dose. For example, the time interval may be between about 200 msec and about 10 msec.

The calculation of dose may also include calculating, for each of the sequential time intervals, a partial dose that is further based upon a latent heat and a specific heat of the material. For example, as described in greater detail herein, constants may be empirically or theoretically (e.g., from the latent heat and/or specific heat of the material being vaporized) and may be initially provided to the devices described herein, or may be periodically updated (e.g., in a calibration step) the any of these devices.

In general, the calculations of partial dose (vapor mass) being delivered by the device may be based on the mass/energy balance in the material being vaporized by balancing the energy put into the material by the heater (e.g., joule heating coil), including the change in energy due to evaporation, the change in heat as it is absorbed by the material to be vaporized, and the energy lost from the system via heat transfer. As described by the inventors herein, this may be expressed with surprising accuracy in terms of the energy (power) applied to the heater and the temperature just before and during/after vaporization of the vaporizable material. Variations in the structure of the vaporizer (heater shape, material, size, etc.) and the material being vaporized may be accounted for as constants and ignored (e.g., providing a unit-less or self-referencing value). For example, the steps of calculating, for each of the sequential time intervals, a partial dose may include subtracting from a first constant times the power delivered by the heater controller to the heater to vaporize the vaporizable material during the partial dose time interval, a second constant times the temperature of the vaporizable material being vaporized during the partial dose time interval and a third constant times the temperature of the vaporizable material being vaporized before the partial dose time interval. Alternatively, the steps of calculating, for each of the sequential time intervals, a partial dose may include subtracting from a first constant times the power delivered by the heater controller to the heater to vaporize the vaporizable material during the partial dose time interval, a different second constant times the difference between the temperature of the vaporizable material being vaporized during the partial dose time interval and the temperature of the vaporizable material being vaporized before the partial dose time interval, and a different third constant times the temperature of the vaporizable material being vaporized before the partial dose time interval.

In general, calculating a partial dose may use the temperature of the vaporizable material being vaporized during the partial dose time interval and the temperature of the vaporizable material being vaporized before the partial dose time interval comprises using an electrical property of the heater that is proportional to the temperature of the heater as the temperature of the vaporizable material being vaporized during the partial dose time interval. Thus, the temperature referred to in any of the calculation steps described herein (e.g., the temperature of the vaporizable material being vaporized during the partial dose time interval and the temperature of the vaporizable material being vaporized before the partial dose time interval) may refer to any value that is proportional to the actual temperature (e.g., using a temperature coefficient of resistance value to determine a value proportionally related to temperature, without requiring the conversion (using constants determined from the system to convert to ° C. or ° F.).

In general the methods and apparatuses described herein may implement the resulting dose information (or partial, running or summed dose information), e.g., to report and/or control operation of the apparatus or transmit to a secondary (e.g., remote) apparatus. For example, any of these methods may also include alerting the user when the total dose of vapor delivered during the time period meets or exceeds a preset threshold. Any of these methods may also include disabling the device when the total dose of vapor delivered during the time period meets or exceeds a preset threshold. Any of these methods (or devices configured to implement them) may further include calculating and displaying a cumulative total dose of vapor delivered over a session period that includes the time period. Thus, the total running dose over multiple puffs (each puff may be considered a time period, or the time period may an entire session in which the apparatus is turned on for vaporizing the material, or multiple on periods until reset by the user).

In general, any of these methods may include detecting a user's puff on the vaporizer device, wherein the time period corresponds to a duration of the detected user's puff.

Any appropriate material to be vaporized (vaporizable material) may be used. In general, the vaporizable material may be a liquid. The vaporizable material may comprise any active ingredient(s). For example, the vaporizable material may comprise a tobacco-based material. The vaporizable material may comprise a botanical. The vaporizable material may comprise a nicotine compound. The vaporizable material may comprise a cannabinoid. The vaporizable material may comprise one or more of: cetirizine, ibuprofen, naproxen, omeprazole, doxylamine, diphenhydramine, melatonin, or meclizine. The vaporizable material may comprise one or more of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, or mometasone and formoterol. The vaporizable material may comprise one or more of: a polyphenol, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, or Vitamin D. The vaporizable material may comprise a nicotine salt, glycerin, and propylene glycol.

As mentioned, the vaporized dose predictor unit may be part of a controller. In some variations, both the vaporized dose predictor and the heater controller are part of the same controller. In some variations the vaporized dose predictor and the heater controller are separate.

Another example of the methods of determining a dose of a vaporizable material delivered to a user of a vaporizing device over a time period as described herein (e.g., wherein the time period comprises a plurality of sequential time intervals, and wherein the vaporizing device includes a heater controller, a heater, a source of the vaporizable material and a vaporized dose predictor unit) may include: transmitting a power delivered by the heater controller to the heater at each of the plurality of sequential time intervals from the power controller to the vaporized dose predictor unit; calculating, for each of the sequential time intervals, a partial dose, wherein the partial dose is calculated from the power delivered by the heater controller to the heater to vaporize the vaporizable material during each of the plurality of sequential time intervals, a temperature of the vaporizable material being vaporized during each of the plurality of sequential time intervals, and a temperature of the vaporizable material being vaporized before each of the plurality of sequential time intervals; and summing the calculated partial doses in the vaporized dose predictor unit to determine a total dose of vapor delivered during the time period.

Any of these methods may also include transmitting the temperature of the vaporizable materials being vaporized during each of the plurality of sequential time intervals from the power controller to the vaporized dose predictor unit.

Another example of a method of determining a dose of a vaporizable material delivered to a user of a vaporizing device over a time period (e.g., wherein the time period comprises a plurality of sequential time intervals, and wherein the vaporizing device includes a heater controller, a heater, a source of the vaporizable material including an active ingredient, and a vaporized dose predictor unit) may include: calculating, for each of the sequential time intervals, a partial dose, wherein the partial dose is calculated from a power delivered by the heater controller to the heater to vaporize the vaporizable material during a partial dose time interval, a temperature of the vaporizable material being vaporized during the partial dose time interval, and a temperature of the vaporizable material being vaporized immediately before the partial dose time interval; summing the calculated partial doses in the vaporized dose predictor unit to determine a total dose of vapor delivered during the time period; and determining an amount of active ingredient delivered to the user based on the total dose of vapor delivered.

A method of determining an amount of vapor delivered to a user of a vaporizing device may include: measuring an amount of power delivered from a power source of the vaporizer device over a first period of time; measuring a temperature of a material being vaporized in the vaporizer device over the first period of time; and determining an amount of vapor delivered to the user during the first period of time based upon the measured amount of power and a change in the measured temperature during the first period of time.

Any of these methods may also include detecting an amount of active ingredient delivered to the user based upon the determined amount of vapor. The measuring step may be performed at any appropriate frequency, such as a frequency of between 5 Hz and 50 Hz within the first period of time. The measuring steps may be performed at a frequency of between 10 Hz and 30 Hz within the first period of time.

As mentioned above, determining the amount of vapor delivered to the user during the first period of time may be further based upon a latent heat and a specific heat of the material.

In any of these methods, determining the amount of vapor delivered to the user during the first period of time comprises calculating based upon the formula:

$$\Delta m_{vap, cumulative} = \sum_{i=1}^{i=n} a[Pi - b(T_i - T_{i-1}) - cT_i]$$

where $\Delta m_{vap, cumulative}$ is the total amount of vapor delivered to the user, a is a constant, b is a constant, c is a constant, P is the measured power, and $T_i$ is the measured temperature from the first period of time, and $T_{i-1}$ is a measured temperature from an immediately preceding time period.

Any of these methods may also include alerting the user when the determined amount of vapor delivered to the user meets or exceeds a preset vapor threshold, and/or disabling the device when the determined amount of vapor meets or exceeds a preset vapor threshold.

Any of these methods may also include detecting a user's puff on the vaporizer device, wherein the measuring steps are performed only during the detected puff.

As mentioned above, in any of the methods described herein, appropriate material to be vaporized (vaporizable material) may be used. In general, the vaporizable material may be a liquid. The vaporizable material may comprise any active ingredient(s). For example, the vaporizable material may comprise a tobacco-based material. The vaporizable material may comprise a botanical. The vaporizable material may comprise a nicotine compound. The vaporizable material may comprise a cannabinoid. The vaporizable material may comprise one or more of: cetirizine, ibuprofen, naproxen, omeprazole, doxylamine, diphenhydramine, melatonin, or meclizine. The vaporizable material may comprise one or more of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, or mometasone and formoterol. The vaporizable material may comprise one or more of: a polyphenol, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, or Vitamin D. The vaporizable material may comprise a nicotine salt, glycerin, and propylene glycol.

Also described herein are vaporization apparatuses, such as devices and systems, configured to determine a dose of the vapor being delivered. For example, a vaporizer device may include: a heater controller; a heater coupled to the heater controller so that the heater controller applies power to the heater; a source of vaporizable material; and a vaporized dose predictor unit receiving input from the heater controller, wherein the vaporized dose predictor is configured to determine a dose of vapor delivered to a user during a time period based upon: an amount of power delivered by the heater controller to the heater to vaporize the vaporizable material during each of a plurality of partial dose time intervals within the time period, a temperature of the vaporizable material being vaporized during each partial dose time interval, and a temperature of the vaporizable material being vaporized before each partial dose time interval.

Any of these devices may also include an output configured to present the amount of vapor delivered by the user during the time period.

Any appropriate output may be used, including a video display, LED, speaker, wireless transmitter, etc. Any of the apparatuses described herein may include a temperature sensor configured to sense a temperature of the vaporizable material being vaporized during each partial dose time interval. As described herein, the temperature sensor may be a separate and/or dedicated (e.g., thermistor) or it may determine the temperature (e.g., of the heater and/or the material being heated) based on the relative resistance of the heater itself.

As mentioned, the vaporized dose predictor unit may include a controller. For example, the vaporized dose predictor unit may be integral with the heater controller. The vaporized dose predictor may be configured to determine the amount of vapor delivered as dose of vapor delivered. The vaporized dose predictor may be configured to determine an amount of active ingredient delivered to the user based on the dose of vapor delivered.

In any of the apparatuses described herein, the partial dose time intervals may each be between about 200 msec and about 10 msec.

The vaporized dose predictor unit may be configured to calculate, for each of the partial dose time intervals, a partial dose by subtracting from a first constant times the power delivered by the heater controller to the heater to vaporize the vaporizable material during the partial dose time interval, a second constant times the temperature of the vaporizable material being vaporized during the partial dose time interval and a third constant times the temperature of the vaporizable material being vaporized before the partial dose time interval.

In general, the vaporized dose predictor unit may be configured to determine the amount of vaporizable material delivered to the user.

As described herein, the vaporized dose predictor unit is configured to use an electrical property of the heater that is proportional to the temperature of the heater as the temperature of the vaporizable material being vaporized during the partial dose time interval.

Any of these apparatuses may include an alarm configured to alert the user when the total dose of vapor delivered during the time period meets or exceeds a preset threshold. Any of these apparatuses may include dose control logic configured to disable the device when the total dose of vapor delivered during the time period meets or exceeds a preset threshold.

Any of these apparatuses may also include a puff detector configured to detect a user puffing on the device. In some variations, the vaporized dose predictor unit may be configured to set the time period as a duration of a detected user's puff (e.g., between 0.5-15 sec, between 0.5-20 sec, between 0.5 to 10 seconds, etc.).

The source of vaporizable material may be a liquid or a solid or a gel. The vaporizable material is preferably a liquid.

Other methods and apparatus variations are also described. For example, described herein are methods for quantifying and controlling an amount of a vapor and/or one or more material(s) within the vapor that is delivered to a user from a reservoir of vaporizable material in an electronic vaporizer device. The electronic vaporizer device may include a puff sensor, a power source (e.g., battery, capacitor, etc.), a heating element controller, and a heating element. A separate temperature sensor may also be included, or it may be part of the heating element controller, which may estimate temperature of the heating element (e.g., resistive coil, etc.) based on a change in resistance due to temperature (e.g., TCR), and may therefore include a reference resistor. One or more additional temperature sensors may also be included. These apparatuses may also include a vaporized dose predictor unit, which may be separate from (and may receive inputs from) the temperature controller or it may be integrated with it. In some variations the apparatus also includes an alert unit and/or a controlling logic for controlling operation of the apparatus based on the determined/estimated dosage (e.g., turning off, triggering an alert, etc.).

For example, a method of operating the device may include: (optionally) a puff sensor detecting a user's puff, the heating element controller measuring an amount of power delivered from the power source during the user's puff (e.g., at multiple discrete time intervals during the puff); the temperature sensor measuring a temperature or a temperature profile of the material being vaporized (e.g., at or near the heating element) during the user's puff; the vaporized dose predictor calculating the amount of the vapor delivered to the user from the vaporizable material based upon the amount of the power and the temperature during the user's puff, or based upon the amount of the power and the temperature profile during the user's puff; and a) engaging the alert unit to alert the user when the amount of the vapor delivered meets or exceeds a preset vapor amount threshold for the user's puff, or when a cumulative amount of the vapor delivered from a plurality of puffs meets or exceeds a preset vapor amount threshold, or b) implementing the controlling logic to disable or modify an output of one or more features of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b). In certain embodiments, the method comprises storing a plurality of measurements of temperature, temperature profiles, amount of power delivered, or a combination thereof, in a memory unit. In certain embodiments, the method comprises adjusting the preset vapor amount threshold from one puff to the next, based on the amount of the vapor delivered to the user by the user's prior puff. In certain embodiments, the electronic vaporizer device comprises a timer, and the method may comprise engaging the timer to measure a puff duration. In certain embodiments, the method comprises storing a plurality of measurements of temperature, temperature profiles, amount of power delivered, puff duration or a combination thereof in a memory unit. In certain embodiments, the method comprises normalizing the amount of the vapor delivered to the user to the puff duration. In certain embodiments, the method comprises attaching a separate pod to the device, the separate pod configured to hold a vaporizable material. In certain embodiments, the method comprises calculating the amount of the vapor delivered to a user from the vaporizable material in milligrams of total particulate matter. In certain embodiments, the method comprises calculating the amount of the vapor delivered to a user from the vaporizable material in milligrams of an active ingredient. In certain embodiments, the method comprises adjusting the preset vapor amount threshold. In certain embodiments, the electronic vaporizer device comprises a heating reservoir distinct from the heating element, and the method comprises preheating a vaporizable material to a preset temperature. In certain embodiments, the vaporizable material is a liquid, viscous liquid, wax or loose-leaf material. In certain embodiments, the vaporizable material is a tobacco-based material. In certain embodiments, the vaporizable material is a botanical. In certain embodiments, the vaporizable material is a medicinal compound. In certain embodiments, the vaporizable material is nicotine. In certain embodiments, the vaporizable material is a cannabinoid. In certain embodiments, the vaporizable material is *Cannabis*. In certain embodiments, the method comprises adjusting a type of the vaporizable material. In certain embodiments, the method comprises adjusting the type of the vaporizable material to a liquid, viscous liquid, wax or loose-leaf material. In certain embodiments, the method comprises adjusting the type of the vaporizable material to a tobacco-based material. In certain embodiments, the method comprises adjusting the type of the vaporizable material to a botanical. In certain embodiments, the method comprises adjusting the type of the vaporizable material to a medicinal compound. In certain embodiments, the method comprises adjusting the type of the vaporizable material to nicotine. In certain embodiments, the method comprises adjusting the type of the vaporizable material to a cannabinoid. In certain embodiments, the method comprises adjusting the type of the vaporizable material to *Cannabis*. Adjusting the vaporizable material may include adjusting the apparatus or method to account for the change in constants and/or calibrating the apparatus to account for changes in the constants that may be used to give a calibrated (e.g., mass or mass/time) output, as described in greater detail herein.

In certain embodiments, the alert unit comprises a piezoelectric speaker, and the method comprises alerting the user by activating the piezoelectric speaker to produce an audible sound when the amount of the vapor delivered to the user meets or exceeds the preset vapor amount threshold. In certain embodiments, the alert unit comprises a light emitting diode, and the method comprises alerting the user by illuminating the light emitting diode when the amount of the vapor delivered to the user meets or exceeds the preset vapor amount threshold. In certain embodiments, the alert unit comprises a vibration motor, and the method comprises alerting the user by activating the vibration motor when the amount of the vapor delivered to the user meets or exceeds the preset vapor amount threshold. In certain embodiments, the controlling logic comprises a software module. In certain embodiments, the controlling logic comprises a hardware element. In certain embodiments, the electronic vaporizer device comprises a display unit, wherein the method comprises providing feedback to the user via the display. In certain embodiments, the electronic vaporizer device is a single-use electronic vaporizer device. In certain embodiments, the electronic vaporizer device is provided to an analytical smoking machine.

In a certain embodiment provided herein, is an electronic vaporizer device configured to quantify and control an amount of a vapor delivered to a user from a vaporizable material in the electronic vaporizer device, wherein the electronic vaporizer device comprises: a puff sensor configured to detect a user's puff; a heating element controller configured to measure an amount of power delivered from a power source during the user's puff; a temperature sensor configured to measure a temperature or a temperature profile generated by a heating element during the user's puff; a vaporized dose predictor unit configured to calculate the amount of the vapor delivered to the user from the vaporizable material based upon the amount of the power and the temperature during the user's puff or based upon the amount of the power and the temperature profile during the user's puff; and one or more of a) an alert unit configured to alert the user when the amount of vapor delivered meets or exceeds a preset vapor amount threshold for the user's puff, or when a cumulative amount of the vapor delivered from a plurality of puffs meets or exceeds a preset vapor amount threshold, and b) a controlling logic configured to automatically disable one or more feature of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b). In certain embodiments, the electronic vaporizer device comprises a memory unit, configured to store a plurality of measurements of temperature, temperature profile, power delivered, or a combination thereof. In certain embodiments, the electronic vaporizer device comprises a timer configured to determine a puff duration. In certain embodiments, the electronic vaporizer device comprises a memory unit, configured to store a plurality of measurements of temperature, temperature profile, power delivered, puff duration or a combination thereof. In certain embodiments, the electronic vaporizer device is configured to normalize the amount of the vapor delivered to the user to the puff duration. In certain embodiments, the electronic vaporizer device comprises a separate pod attached to the device, the separate pod configured to hold a vaporizable material. In certain embodiments, the electronic vaporizer device is configured to calculate the amount of the vapor delivered to the user from a vaporizable material in milligrams of total particulate matter. In certain embodiments, the electronic vaporizer device is configured to calculate the amount of the vapor delivered to the user from a vaporizable material in milligrams of total particulate matter. In certain embodiments, the electronic vaporizer device is configured to allow adjustment of the preset vapor amount threshold. In certain embodiments, the electronic vaporizer device comprises a heating reservoir distinct from the heating element. In certain embodiments, the electronic vaporizer device comprises a vaporizable material that is a liquid, viscous liquid, wax or loose-leaf material. In certain embodiments, the electronic vaporizer device comprises a vaporizable material that is a tobacco-based material. In certain embodiments, the electronic vaporizer device comprises a vaporizable material that is a botanical. In certain embodiments, the electronic vaporizer device comprises a vaporizable material that is a medicinal compound. In certain embodiments, the electronic vaporizer device comprises a vaporizable material that is nicotine. In certain embodiments, the electronic vaporizer device comprises a vaporizable material that is a cannabinoid. In certain embodiments, the electronic vaporizer device comprises a vaporizable material that is *Cannabis*. In certain embodiments, the electronic vaporizer device is configured to allow adjustment of a type of the vaporizable material. In certain embodiments, the type of the vaporizable material is adjustable to a liquid, viscous liquid, wax or loose-leaf material. In certain embodiments, the type of the vaporizable material is adjustable to a tobacco-based material. In certain embodiments, the type of the vaporizable material is adjustable to a botanical. In certain embodiments, the type of the vaporizable material is adjustable to a medicinal compound. In certain embodiments, the type of the vaporizable material is adjustable to nicotine. In certain embodiments, the type of the vaporizable material is adjustable to a cannabinoid. In certain embodiments, the type of the vaporizable material is adjustable to *Cannabis*. In certain embodiments, the alert unit comprises a piezoelectric speaker. In certain embodiments, the alert unit comprises a light emitting diode. In certain embodiments, the alert unit comprises a vibration motor. In certain embodiments, the controlling logic comprises a software module. In certain embodiments, the controlling logic comprises a hardware element. In certain embodiments, the electronic vaporizer device comprises a display unit, configured to provide feedback to the user. In certain embodiments, the electronic vaporizer device is a single-use electronic vaporizer device. In certain embodiments, the electronic vaporizer device is a vaporizing device.

In a certain embodiment provided herein, is a method, the method comprising an electronic vaporizer device configured to quantify and control an amount of a vapor delivered to a user from a vaporizable material in the electronic vaporizer device, wherein the electronic vaporizer device comprises: a puff sensor configured to detect a user's puff; a heating element controller configured to measure an amount of power delivered from a power source during the user's puff; a temperature sensor configured to measure a temperature or a temperature profile generated by a heating element during the user's puff; a vaporized dose predictor unit configured to calculate the amount of the vapor delivered to the user from the vaporizable material based upon the amount of the power and the temperature during the user's puff or based upon the amount of the power and the temperature profile during the user's puff; and one or more of a) an alert unit configured to alert the user when the amount of vapor delivered meets or exceeds a preset vapor amount threshold for the user's puff, or when a cumulative amount of the vapor delivered from a plurality of puffs meets or exceeds a preset vapor amount threshold, and b) a controlling logic configured to automatically disable one or more feature of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b). In certain embodiments, the electronic vaporizer device comprises a memory unit, configured to store a plurality of measurements of temperature, temperature profile, power delivered, or a combination thereof. In certain embodiments, the electronic vaporizer device comprises a timer configured to determine a puff duration. In certain embodiments, the electronic vaporizer device comprises a memory unit, configured to store a plurality of measurements of temperature, temperature profile, power delivered, puff duration or a combination thereof. In certain embodiments, the electronic vaporizer device is configured to normalize the amount of the vapor delivered to the user to the puff duration. In certain embodiments, the electronic vaporizer device comprises a separate pod attached to the device, the separate pod configured to hold a vaporizable material. In certain embodiments, the electronic vaporizer device is configured to calculate the amount of the vapor delivered to the user from a vaporizable material in milligrams of total particulate matter. In certain embodiments, the electronic vaporizer device is configured to calculate the amount of the vapor delivered to the user from a vaporizable material in milligrams of total particulate matter. In certain embodiments, the electronic vaporizer device is configured to allow adjustment of the preset vapor amount threshold. In certain embodiments, the electronic vaporizer device comprises a heating reservoir distinct from the heating element. In certain embodiments, the electronic vaporizer device comprises a vaporizable material that is a liquid, viscous liquid, wax or loose-leaf material. In certain embodiments, the electronic vaporizer device comprises a vaporizable material that is a tobacco-based material. In certain embodiments, the electronic vaporizer device comprises a vaporizable material that is a botanical. In certain embodiments, the electronic vaporizer device comprises a vaporizable material that is a medicinal compound. In certain embodiments, the electronic vaporizer device comprises a vaporizable material that is nicotine. In certain embodiments, the electronic vaporizer device comprises a vaporizable material that is a cannabinoid. In certain embodiments, the electronic vaporizer device comprises a vaporizable material that is *Cannabis*. In certain embodiments, the electronic vaporizer device is configured to allow adjustment of a type of the vaporizable material. In certain embodiments, the type of the vaporizable material is adjustable to a liquid, viscous liquid, wax or loose-leaf material. In certain embodiments, the type of the vaporizable material is adjustable to a tobacco-based material. In certain embodiments, the type of the vaporizable material is adjustable to a botanical. In certain embodiments, the type of the vaporizable material is adjustable to a medicinal compound. In certain embodiments, the type of the vaporizable material is adjustable to nicotine. In certain embodiments, the type of the vaporizable material is adjustable to a cannabinoid. In certain embodiments, the type of the vaporizable material is adjustable to *Cannabis*. In certain embodiments, the alert unit comprises a piezoelectric speaker. In certain embodiments, the alert unit comprises a light emitting diode. In certain embodiments, the alert unit comprises a vibration motor. In certain embodiments, the controlling logic comprises a software module. In certain embodiments, the controlling logic comprises a hardware element. In certain embodiments, the electronic vaporizer device comprises a display unit, configured to provide feedback to the user. In certain embodiments, the electronic vaporizer device is a single-use electronic vaporizer device. In certain embodiments, the electronic vaporizer device is a vaporizing device.

BRIEF DESCRIPTION OF THE DRAWINGS

The novel features of the invention are set forth with particularity in the description. Like numbers refer to like elements throughout the description of the figures. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 1B-1D shows one example of a vaporizing apparatus as described herein, in cross-sectional, side and top views, respectively.

FIG. 3 is a table showing a comparison between actual measured dosage (total particulate matter, or TPM, vaporized) and the dosage predicted as described herein based on discrete estimates at multiple time intervals during a puff (inhalation) using the power applied to the vaporization element (heater) and the temperature of the vaporization element or the temperature of the material being vaporized at the start and finish of each of the multiple time intervals.

FIG. 4 is another table comparing measured and estimated doses (in TPM) during a trail in humans using one variation of the methods described herein.

FIG. 7 schematically illustrates one example of a heater (atomizer) and vaporizable material reservoir for forming a vapor as described herein. In this example the heater includes a wick connected to the reservoir and a heating element in contact with the wick; the wick and heating element extend in an airflow path for drawing out the vapor formed. In this example, the walls of the reservoir are heated.

DETAILED DESCRIPTION

Figure 1A:
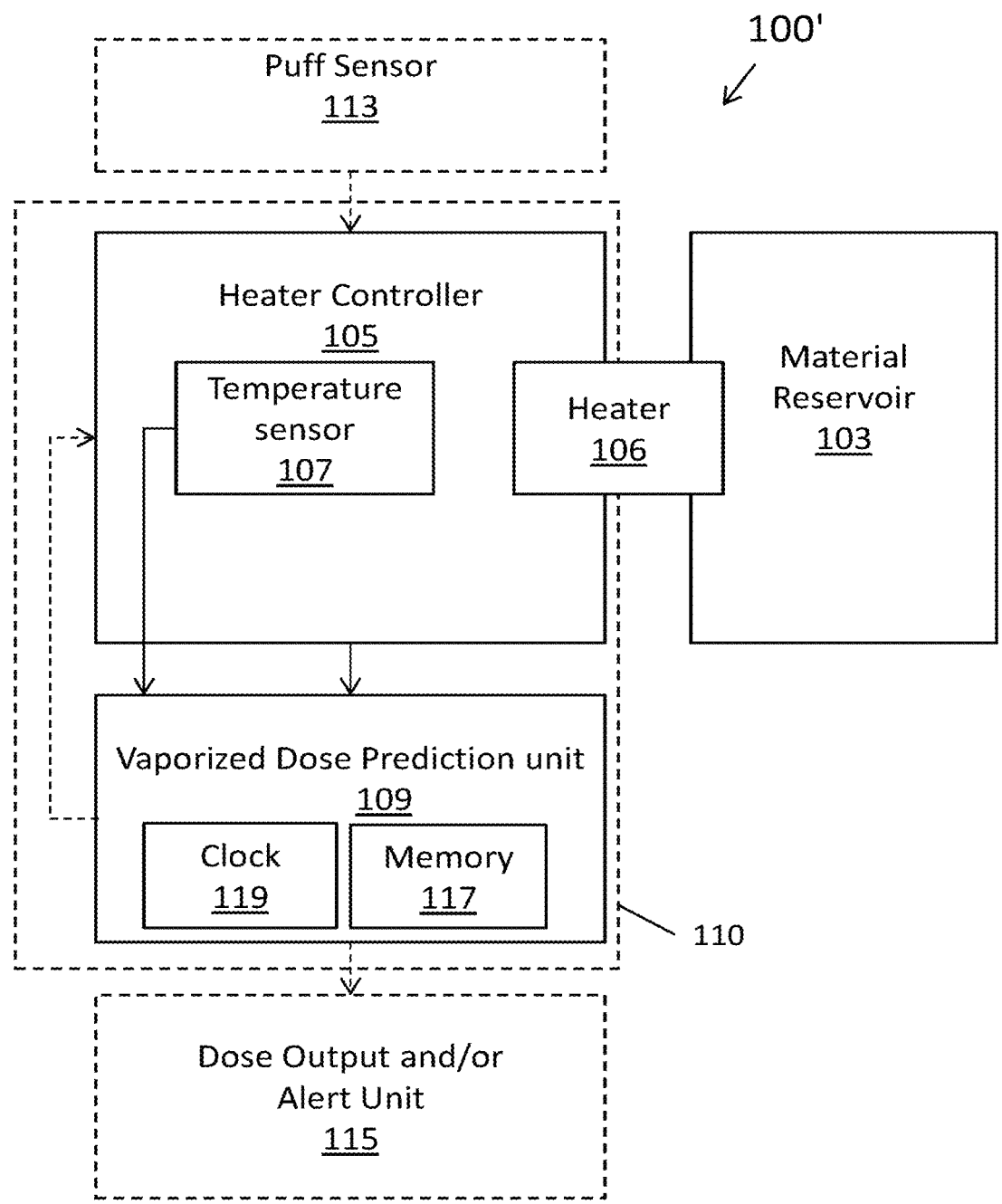
FIG. 1A is a schematic of a vaporizing apparatus including a vaporized dose estimation/prediction unit.

The present disclosure provides a method for quantifying and controlling an amount of a vapor delivered to a user from a vaporizable material in an electronic vaporizer device comprising measuring the vaporizable material intake evaporated, aerosolized or vaporized from a vaporizable material in a vaporizing device or electronic vaporizer device relative to power consumed during vaporization and temperature produced during vaporization. Also provided in this disclosure are calibration methods that may include establishing a relationship of total particulate matter (TPM) vaporized from a vaporizable material as a function of temperature generated and power consumed. Calibration may be performed one time (e.g., at a factory) or it may be performed by the user. Alternatively or additionally, the user may be requested or required to perform a calibration step that include inputting an identifier of the material be vaporized (e.g., selecting or inputting the material and/or concentration, or a reference identified, such as a lot number or the like that can be linked to the material being vaporized). For example, a user may scan (e.g., using a QR code, bar code, or equivalent) the vaporizable material or packing and/or inserts affiliated with the vaporizable material. In some variations the apparatus includes a look-up table corresponding to a variety of vaporizable materials that may include values for calibrating the apparatus, including the constants referred to herein that may be used to calibrate the mass of the vapor and/or one or more components (e.g., active agents/active ingredients) in the vaporizable material.

The term "vape" or "vaping", as used herein, refers to the action of or the experience of using a vaporization device, such as an electronic vaporizer device for the delivery of vapor to a user.

The term "puff" refers to the process of removing vapor from a vaporization device or e-vaporizer device using a suction mechanism. In certain embodiments, the suction mechanism is a user. In certain embodiments, the suction mechanism is an analytical smoking machine. Commonly used synonyms for puff are drag, draw, hit, suck, pull, inhale, or smoke for example.

As used herein a dose may refer to the amount or quantity of the vapor and/or material (e.g., active ingredient(s), etc.) taken at a particular time. The dose may be quantified as a mass, or a mass/time, depending on the context. The dose may be dose/puff.

The term "puff duration" as used herein, refers to a length of time during which a vaporization device or electronic vaporizer device is coupled to a suction mechanism. In certain embodiments, the suction mechanism is a user. In certain embodiments, the suction mechanism is an analytical smoking machine. In certain embodiments, suction is provided through a mouthpiece.

The term "puff volume" as used herein, refers to a volume leaving a vaporizer device (e.g. standard reference vaporizer device, test vaporizer device, electronic vaporizer device, or vaporization device.). The volume can comprise one or more gas, solid, and/or liquid species. The puff volume can comprise an amount in ml (or cc) of air or aerosol drawn through a device, for example, either an analytical smoke machine or an electronic vaporizer device.

The term "puff frequency" as used herein refers to a number of puffs in a certain time period. In certain embodiments, the puff frequency is calculated using a mean number of puffs per a unit of time that is milliseconds, seconds, minutes or hours. In certain embodiments, the puff frequency is calculated using 1, 2, 3, 4, 5, 6, 7, 8, 9, or 10 consecutive puffs. In certain embodiments, the puff frequency is calculated using 10, 20, 30, 40, 50, 60, 70, 80, 90, or 100 consecutive puffs. In certain embodiments, the puff frequency is 1 puff every 1 second. In certain embodiments, the puff frequency is 1 puff about every 2 seconds. In certain embodiments, the puff frequency is 1 puff about every 3 seconds. In certain embodiments, the puff frequency is 1 puff about every 4 seconds. In certain embodiments, the puff frequency is 1 puff about every 5 seconds. In certain embodiments, the puff frequency is 1 puff about every 6 seconds. In certain embodiments, the puff frequency is 1 puff about every 7 seconds. In certain embodiments, the puff frequency is 1 puff about every 8 seconds. In certain embodiments, the puff frequency is 1 puff about every 9 seconds. In certain embodiments, the puff frequency is 1 puff every 10 seconds. In certain embodiments, the puff frequency is 1 puff about every 15 seconds. In certain embodiments, the puff frequency is 1 puff about every 20 seconds. In certain embodiments, the puff frequency is 1 puff about every 25 seconds. In certain embodiments, the puff frequency is 1 puff about every 30 seconds. In certain embodiments, the puff frequency is 1 puff about every 35 seconds. In certain embodiments, the puff frequency is 1 puff about every 40 seconds. In certain embodiments, the puff frequency is 1 puff about every 45 seconds. In certain embodiments, the puff frequency is 1 puff about every 50 seconds. In certain embodiments, the puff frequency is 1 puff about every 55 seconds. In certain embodiments, the puff frequency is 1 puff about every 60 seconds.

The term "total particulate matter (TPM)", as used herein, refers to an amount of matter removed from an organic material by evaporation, vaporization or aerosolization by puffing on vaporizer or electronic vaporizer device; and as used herein, can be synonymous to the phrase "mass vaporized", or "mass aerosolized", or "$m_{vap}$" or "evaporated mass."

The term "analytical smoking machine", as used herein refers to a tool that can puff on a cigarette or vaporizer device with a specified and controlled puff volume and duration.

The term "vaporizable material", as used herein, refers to a formulation of material, including in particular an organic material or botanical that is placed in a vaporization device, electronic vaporizer device, or pod (or a proprietary container) that houses the formulation. The vaporizable material can be a liquid, oil, or wax. In certain embodiments, the vaporizable material is a loose leaf substance. In certain embodiments, the vaporizable material can contain medicinal properties that ameliorate symptoms of a medical condition. In certain embodiments, the vaporizable material can contain a recreational drug.

As used herein, the term "vapor" refers to the output of a vaporizer device, including a chemical compound or mixture of chemical compounds in the gas phase or as an aerosol.

The term "memory unit," as used herein, refers to a non-transitory computer readable medium, software or algorithm for data storage. In certain embodiments, a memory unit is a solid state device. In certain embodiments, a memory unit is internal to the device. In certain embodiments, a memory unit stores data in random access memory (RAM). In certain embodiments, a memory unit is a hard disk, tape drive, or other external device. In certain embodiments, a memory unit refers to a device configured as a permanent holding place for digital data, until purposely erased. A memory unit also refers to devices configured as non-volatile memory chips such as flash, Read-Only memory (ROM) and/or Electrically Erasable Programmable Read-Only Memory (EEPROM).

The term "adjusting," as used herein, may refer to choosing a pod, choosing an operating parameter, choosing a type of a vaporizable material, choosing a dosage in an amount of TPM, an amount of an active ingredient, or a percentage, ratio or fraction of TPM or an active ingredient, and/or may refer to calibrating the apparatus.

The term "nicotine" as used herein refers to nicotine, nicotine salts of organic acid, and common nicotine derivatives such as; norcotinine, nornicotine, nicotine N-oxide, cotinine N-oxide, 3-hydroxycotinine and 5-hydroxycotinine.

The term "cannabinoid" refers to plant based or synthetic chemical compounds capable of acting on cannabinoid receptors and inducing a biological effect. Cannabinoids include acids, salts, and bioactive stereo isomers.

The term "*Cannabis*" refers to plants of the genus *Cannabis* and loose-leaf products or extracts thereof.

In general, described herein are methods for quantifying and, in some variations, controlling an amount of a vapor delivered to a user from a vaporizable material in an electronic vaporizer device. In some variations, the electronic vaporizer device comprises (optionally): a puff sensor, a power source, a heating element controller, a heating element, a temperature sensor, a vaporized dose predictor unit, an alert unit and/or a controlling logic. A method for quantifying and/or controlling may include: (optionally) a puff sensor detecting a user's puff, the heating element controller measuring an amount of power delivered from the power source during the user's puff; the temperature sensor measuring a temperature or a temperature profile generated by the heating element during the user's puff; the vaporized dose predictor unit calculating the amount of the vapor delivered to the user from the vaporizable material based upon the amount of the power and the temperature during the user's puff, or based upon the amount of the power and the temperature profile during the user's puff and a) engaging the alert unit to alert the user when the amount of the vapor delivered meets or exceeds a preset vapor amount threshold for the user's puff, or when a cumulative amount of the vapor delivered from a plurality of puffs meets or exceeds a preset vapor amount threshold, or b) implementing the controlling logic to disable or modify an output of one or more features of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b).

As will be apparent when described in greater detail below, the puff sensor is not necessary; the apparatus and methods described herein will simply return a zero value for the dose delivered when the user is not puffing, since the vaporizer will not form the vapor in the absence of puffing. In addition, the methods described may be considered generally discrete, in that the estimation of vapor dose is performed at discrete intervals forming partial doses that may later be added up to form the overall dose delivered. This configuration may, in part, allow these methods and apparatuses to function with surprising accuracy despite highly variable puffing durations and profiles.

Also provided herein are electronic vaporizers configured to quantify and/or control an amount of a vapor delivered to a user from a vaporizable material in the electronic vaporizer device, wherein the electronic vaporizer device may comprise any of: (optionally) a puff sensor configured to detect a user's puff; a heater controller (also referred to as a heating element controller) configured to determine an amount of power delivered from a power source during the user's puff; a temperature sensor (which may be a direct sensor such as a thermistor, or it may be a temperature sensing unit that determines the temperature, e.g., of the heater, based on electrical properties of the heater) configured to determine a temperature or a temperature profile generated by a heating element during the user's puff; a vaporized dose predictor (also referred to as a vaporized dose predictor unit or circuitry) that calculates the amount of the vapor delivered to the user from the vaporizable material based upon the power applied to the heater and the temperature of the heater (which may be an estimate of the temperature of the vaporizable material as it is vaporized) during a user's puff, or based upon the amount of the power and the temperature profile during the user's puff; and one or more of: a) an alert unit configured to alert the user when the amount of vapor delivered meets or exceeds a preset vapor amount threshold for the user's puff, or when a cumulative amount of the vapor delivered from a plurality of puffs meets or exceeds a preset vapor amount threshold, and b) a disabling unit configured to automatically disable one or more feature of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b).

FIG. 1A is a schematic illustration of one example of an electronic vaporization device 100' including a vaporized dose predictor unit 109. In general any of the vaporizer apparatuses described herein may include a heater controller 105, a heater 106, a source of vaporizable material 103, a power source (e.g., battery, not shown), and a vaporized dose predictor unit 109. The vaporized dose predictor unit 109 may include a clock 119 and/or a memory (memory unit) 117, or these elements may be part of an overall circuitry including a processor 110 which communicates with the vaporized dose prediction unit.

The heater may be any appropriate heater, including resistive heaters such as a resistive coil. The heater is typically coupled to the heater controller so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater. The controller forming or including the heater controller may also include additional controllers/processors and executing logic 110, such as the vaporized dose predictor unit, alert/alarm logic, and/or temperature detector/sensor 107, or these components may be separate.

Any a source of vaporizable material may be used, including a reservoir (e.g., well, pod, cartridge, or the like), which includes the material to be vaporized. The material to be vaporized may include a carrier and one or more active ingredients, as discussed in greater detail herein.

In general, the vaporized dose predictor unit is configured to divide up a time period (e.g., during a single puff) into a plurality of sequential time intervals, which may be referred to as partial dose intervals, and determine the partial dose (or mass) of vapor produced during each partial dose interval. The vaporized dose predictor unit may then sum these up to determine the actual dose produced and presumably delivered to the user. Thus, the device, including the vaporized dose predictor unit may include a timer or clock 117 and can generate intervals of any appropriate duration within a time period (e.g., between 10 msec and 200 msec). Thus, the vaporized dose predictor unit may sample at a frequency related to the duration of the time intervals (e.g., between 5 Hz and 100 Hz, etc., between 5 Hz and 120 Hz, between 5 Hz and 140 Hz, between 5 Hz and 150 Hz, between 5 Hz and 180 Hz, between 5 Hz and 200 Hz, between 5 Hz and 300 Hz, etc.). The vaporized dose predictor unit generally bases the calculation of each partial dose on input from the heater controller, which may include the power applied before or at the start of each partial dose interval. The vaporized dose predictor unit also receives an input proportional to the temperature at the start and at the end of each partial dose interval (e.g., the temperature or a value proportional to the temperature at the end of the immediately previous partial dose interval). In variations in which the temperature is an average value for each dose interval, the vaporized dose predictor unit may receive the temperature (or a proportional value) for a dose interval and the temperature (or a proportional value) of the dose interval immediately preceding it. The vaporized dose predictor unit may then use this applied power and temperature information to calculate the dose (e.g., mass) of vapor during that interval, as will be described in greater detail below. These interval values (dose interval values) may be summed over the entire time period to determine the overall dose of vapor generated; the vaporized dose predictor unit may also then convert this dose of vapor to a dose of an active ingredient in the vapor, by, e.g., converting based on the concentration of active ingredient in the vaporizable material. U.S. patent application Ser. No. 14/581,666, filed Dec. 23, 2014 and titled "Vaporization Device Systems and Methods," previously incorporated by reference in its entirety, also describes vaporizers including methods and apparatuses for temperature measurement and control similar to that described above.

As mentioned above, in some variations the temperatures for the vaporizable material being vaporized by the device are determined from the heater, without requiring an additional sensor. For example, the relative change in resistance of the heater (e.g., the temperature coefficient of resistivity) may be used, along with a reference resistor, to approximate the temperature of the heater. Although a conversation factor may be used to convert the ratio of heater resistivity and reference resistivity to an actual temperature value, in some variations the system, and particularly the vaporized dose predictor unit, may use the proportional value directly, without multiplying by a conversion factor. These values are therefore "proportional" to the temperature. For example, any of these apparatuses may include logic for determining the temperature of the heater based on the TCR. The resistance of the heater (e.g., a resistive heater) may be measured ($R_{heater}$) during operation of the apparatus as well as the resistance of a eater, reference ($R_{reference}$) resistor separate from the heater. The ratio of the heater resistance to the reference resistance ($R_{heater}/R_{reference}$) is linearly proportional with the temperature (above room temp) of the heater, and may be directly converted to a calibrated temperature. For example, a change in temperature of the heater relative to room temperature may be calculated using an expression such as $(R_{heater}/R_{reference}-1*(1/TCR))$, where TCR is the temperature coefficient of resistivity for the heater. In one example, TCR for a particular device heater is 0.00014. In determining the partial doses and doses described herein, the temperature value used (e.g., the temperature of the vaporizable material during a dose interval, $T_i$, described in more detail below) may refer to the unitless resistive ratio (e.g., $R_{heater}/R_{reference}$) or it may refer to the normalized/corrected temperature (e.g., in ° C.).

Thus, the vaporized dose predictor unit may be configured to determine a dose of vapor delivered to a user during a time period based upon: an amount of power delivered by the heater controller to the heater to vaporize the vaporizable material during each of a plurality of partial dose time intervals within the time period, a temperature of the vaporizable material being vaporized during each partial dose time interval, and a temperature of the vaporizable material being vaporized before each partial dose time interval. As just mentioned, the temperature of the vaporizable material being vaporized may refer to an input that is proportional to the temperature.

Other optional features shown in FIG. 1A may include a puff sensor 113 and/or dose output 115. The puff sensor typically detects the application of a puff by the user, and may include a pressure sensor, flow sensor, or contact sensor (e.g., lip contact sensor). A dose output may include any appropriate output, including a visual output (e.g., LED, monitor, etc.), audio output (buzzer, tone, etc.), tactile output (vibrator, etc.), or the like. The dose output may act as an alarm or alert to the user, e.g., when a dose threshold has been reached.

FIGS. 1B-1D show an exemplary compact electronic vaporizer device assembly 100, such as an electronic cigarette, medical inhaler, or other inhalation device, for generating an inhalable aerosol. The compact electronic device 100 can include a device body 200 with a cartridge receptacle 210 for receiving a cartridge 300 or a "pod" that can be removably inserted into the device body 200. A mouthpiece 310 allows the user to puff on the device to inhale material aerosolized by the device.

The device body 200 can include a power source 230, such as a rechargeable battery, a printed circuit board (PCB) 240 containing a microcontroller with the operating logic and software instructions for the device, and a puff sensor 270 for sensing when the user is drawing vapor from the device.

The cartridge 300 can include a heater 360 and a material storage compartment 320 configured to store the material to be vaporized. The heater 360 may be powered by the power source 230. In this example, the heater 360 may be used as a temperature sensor as described above and herein, e.g., using the temperature coefficient of resistance (TCR) and a reference resistance. Alternatively or additionally, a separate temperature sensor (e.g., thermistor, etc.) that is in thermal contact with the heater and/or vaporizable material may be used. The temperature sensor may, in general, be configured to measure a temperature of a vaporizable material within the heater 360. The temperature of the heater may be controlled by the microcontroller of the PCB 240.

The device 100 (or any other vaporizable device) can include on-board processing configured to determine an amount of material vaporized and delivered to the user.

Figure 1E:
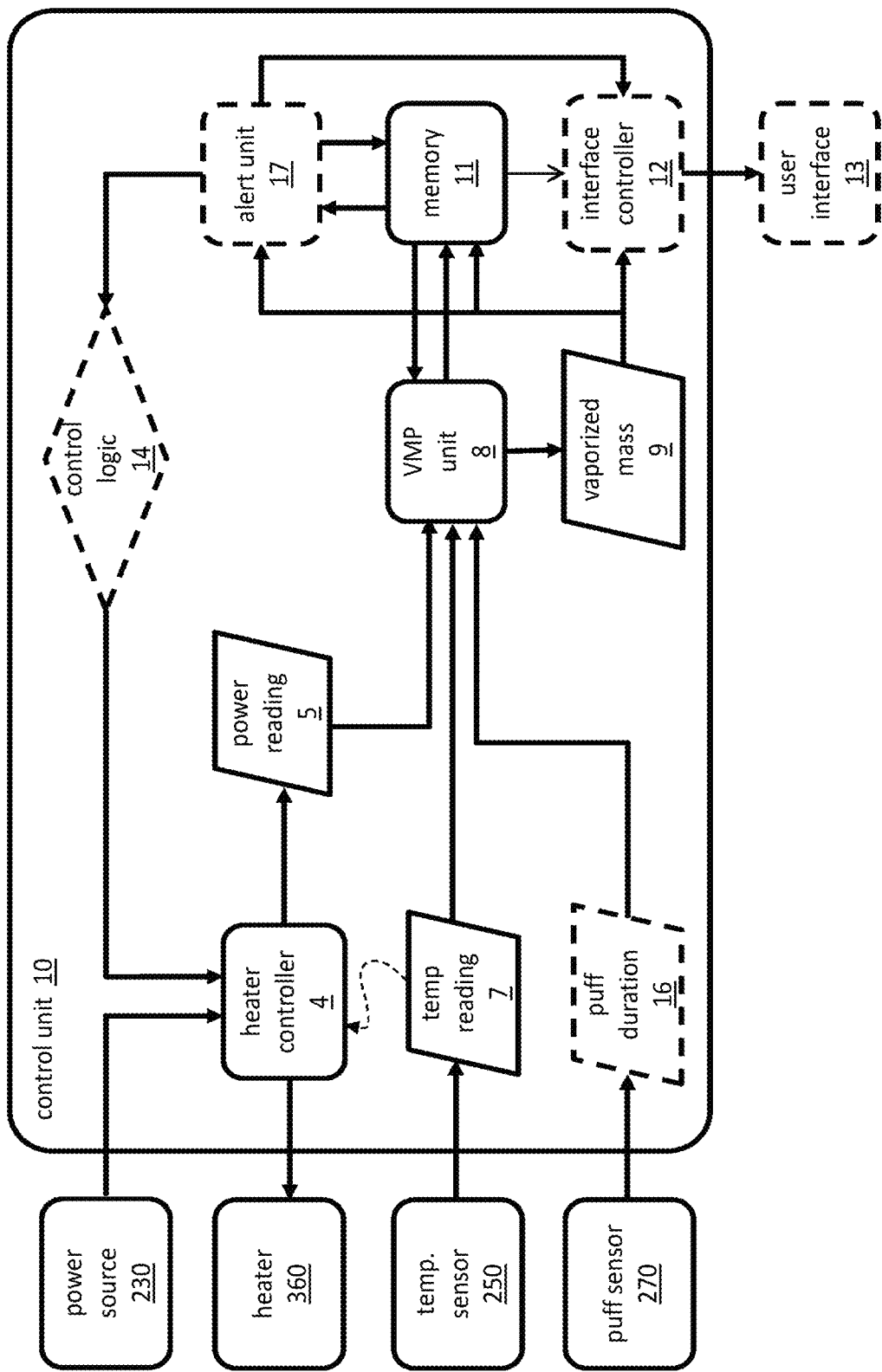
FIG. 1E is an example of an exemplary apparatus able to determine the amount of material vaporized by the device.

FIG. 1E shows a flowchart that represents another exemplary vaporizer apparatus capable of determining the amount of material vaporized within the apparatus (device 100). As shown, the power source 230, heater 360, temperature sensor 250, and puff sensor 270 are communicatively coupled to a control unit 10 (which can be part of one or more printed circuit board(s) 240 shown in FIGS. 1B-1D).

The control unit 10 can include a heating element controller 4, vaporized mass predictor (VMP or VMP unit, which may be a type of vaporized dose estimation/prediction unit) 8, and a memory unit 11. In some embodiments, a user interface 13 on the device can provide the user with information related to the device, such as the amount of vapor inhaled. An interface controller 12 within the control unit can be configured to control the user interface 13. In a certain embodiment, the device additionally comprises an alert unit 17.

To determine an amount of vapor received by the user, the control unit 10 can relay a temperature reading 7 and a power reading 5 during a puff duration 16 (which can be determined by the puff sensor 270) to the VMP unit 8, which can calculate a predicted vaporized mass 9. In certain embodiments, the VMP unit 8 relays the predicted vaporized mass 9 to the memory unit 11. In certain embodiments, the VMP unit 8 relays the predicted vaporized mass to the user interface controller 12. In a certain embodiment, the processor comprises a controlling logic 14 that relays instructions to the heating element controller 4. In a certain embodiment, the method comprises activating an alert unit.

Calculation of Vaporizable Material Vaporized—Exemplary Method

In a certain embodiment, the amount of vapor generated from a vaporizable material within a vaporizing device, such as device 100, can be calculated from the power supplied to a vaporizable material by a power source, and the temperature generated during vaporization. In some embodiments, the amount of vapor generated from a vaporized material can be calculated as a function of energy consumed and temperature generated during vaporization. That is, the power consumed by the power source (such as power source 240), as set by the heater controller (though in some variations it could be measured from the heater or power source) and the temperature of the vaporized material (such as within the chamber 32), as measured by a temperature sensor (such as temperature sensor 250) can be used to determine the amount of vapor generated and/or inhaled.

In some embodiments, the total mass vaporized can be predicted or determined based upon equation 1:

$$\Delta m_{vap,cumulative} = \Sigma_{i=1}^{i=n} a[P_i - b(T_i - T_{i-1}) - cT_i] \quad \text{(equation 1)}$$

where $\Delta m_{vap,cumulative}$ is the total mass vaporized during sampling intervals i=1 to i=n, each interval being of a fixed time increment; $P_i$ is power supplied during interval i; a, b, and c are constants; $T_i$ is temperature reading for interval i; $T_{i-1}$ is temperature reading for interval immediately before the current interval (i−1 immediately prior to interval i). Note that in some variations, the temperature may be temperature relative to room (or starting) temperature and may be expressed as $T_i'$ (e.g., $T'_i$, $T'_{i-1}$, etc.)

An alternative expression of this relationship may be described as:

$$\Delta m_{vap,cumulative} = \Sigma_{i=1}^{i=n} [aP_i - dT_i - eT_{i-1}] \quad \text{(equation 2)}$$

In this example, different coefficient may be used (e.g., d, e); this expression may be more simply implemented using a microcontroller than equation 1, as it has fewer arithmetic functions required, though it is mathematically equivalent.

The coefficients a, b, and c may reflect physical constants whose values can be determined experimentally and can vary depending on the vaporizable material used. For example, the constants a, b, and c can depend upon the latent heat and the specific heat of the material being vaporized. The constants can further depend upon the overall mass of the system that needs to be heated (such as the liquid material and the heater, e.g., a wick and coil). In one exemplary embodiment described below, a is equal to 0.025, b is equal to 367, and c is equal to 30. In another embodiment, a can be equal to 0.18, b can be equal to 2000, and c can be equal to 50. These constants may be determined empirically or based on theoretical values knowing the dimensions and material properties of the vaporizable material and heater.

For example, in some embodiments, the coefficients a, b, and c can be determined by collecting an amount of data and running a mathematical algorithm. For example, an analytical inhalation or smoking machine can be used to test the vaporizing device under one or more conditions. Total particulate matter (TPM) can be collected from the vaporizing device using the analytical inhalation or smoking machine. In some cases, the TPM can be collected on a filter pad. The filter pad can be weighed before and after TPM is collected on the filter such that the weight of the TPM on the filter can be determined. In some embodiments, the empirical determination of (a, b and c) is accomplished by measuring power and temperature over a series of puffs and measuring the cumulative mass lost by the device for those puffs gravimetrically. The mass lost by the device is taken as being equal to total delivered mass of TPM (mg). Best values for a, b, and c are then determined by fitting the above equation to the experimental mass delivery, power and temperature data. Adjustments in the constants (e.g., a, b, c or a, d, e) can be made to accommodate the variance in the type of the device and of the formulation.

One example of a method for determining the values of the constants associated with the relationship between the mass of vapor emitted, power applied to vaporize the material during a particular time interval (e.g., portion of a puff) and the temperature of the material before and after vaporization during that period is described below. In this example, the device may be first weighed. Then, a series of puffs may be taken while logging the power (e.g., at a sampling frequency such as 20 Hz, e.g. between 5 Hz and 100 Hz, 5 Hz and 200 Hz, etc.) and the temperature through the duration of the trial. The device may then be weighed again. This may be repeated many times (e.g., more than 5, 10, 15, 20, 25, 30, 35, 40, 45, 50, 60, 70, 80, 90, 100, 120, 150, 200, etc., or between 5 and 1000, between 10 and 500, between 10 and 200, etc.) to achieve a sufficiently sized data set. In one example, the process is repeated 29 times. The m_vap may then be calculated for each sample by subtracting the final mass from the initial mass. Alternatively, the mass of the vapor may be directly measured, e.g., by applying the vapor onto a filter pad and use the change in mass of the pad to get m_vap; this may be less accurate because some of the vapor might go through the pad or deposit on other surfaces. For simple gravimetric analysis, measuring the device may be preferred.

After collecting all the data, the m_vap estimates, as well as a set of values for temp and power over the duration for each sample may then be used to solve for the constants. For example, in equation (1), the constants a, b, and c may be determined from this data. Alternative expression of the equation (e.g., see equation 2, described below) may be used. For example, the values of a, b, and c may be determined such that $\text{SUM}[t=1 \text{ to } t=n](aP-b(T_i-T_{i-1})-cT_i)$ may be solved to find the best fit to the m_vap that was measured for each sample. As mentioned, this may be performed for any expression of the vapor mass, applied power and temperatures measured. In some variations this may be performed using a gradient descent algorithm, to fit the data to the appropriate equation. A gradient descent algorithm may be beneficial because is computationally cheap to find the optimal values of the constants (e.g., a, b, and c) such that error is minimized. However, any appropriate curve-fitting algorithm or method may be used. In this first example, three different constants are fit to a rather large dataset.

In some embodiments, the time interval i (e.g., the partial dose time interval) can be between 20 ms and 200 ms (e.g., less than 200 msec, 180 msec, 150 msec, 120 msec, 100 msec, 90 msec, 80 msec, 70 msec, 60 msec, 50 msec, 40 msec, 30 msec, 20 msec, 10 msec, etc.). The temperature and power measurements can be taken at a frequency of between 5 and 50 Hz, such as between 10 and 30 Hz, such as at approximately 20 Hz.

In general, the power to may refer to power delivered to heat the vaporizable material (e.g., in some variations, the power applied by the heater controller to the heater) to vaporize the vaporizable material during a partial dose time interval. The power applied may be read directly from the heater controller (e.g., a watts, joules, joules/sec$^2$, volts*volts, volts*volts/resistance, etc.) and/or may be sensed, e.g., using any appropriate power sensor (voltmeter, hall effect sensor, inductive sensor, direct measurement sensor, voltage response measurement sensor, etc.). The power may be detected either immediately before or during the time interval (e.g., partial dose interval), representing the power applied to vaporize the material during that interval. For example, the power used to determine a partial dose may be transmitted from the heater controller simultaneous with applying the power to the heater; in some variations the power ($P_i$) is the power applied during the interval immediately before the interval i (e.g., i−1) because this power is then absorbed by the vaporizable material during the dose interval being measured. Alternative, when the power ($P_i$) may be the power sensed directly or indirectly during the relevant dose interval (i).

Similarly, the temperature measured may be the temperature of the vaporizable material being vaporized during the partial dose time interval ($T_i$). This may be sensed directly or indirectly during, at the start and/or at the end of the dose interval. For intervals that are sufficiently brief, this distinction may be irrelevant. The temperature of the vaporizable material being vaporized before the partial dose time interval may refer to the dose from the immediately prior time interval (e.g., $T_{i-1}$), which may also be the temperature at the start, end or during the prior time interval. Alternatively, in some variations the temperature of the of the vaporizable material being vaporized before the partial dose time interval may refer to the temperature of the material to be vaporized immediately before the Pi is applied (e.g., at the start or just before the start, of the application of power); the temperature of the vaporizable material being vaporized during the partial dose time interval may refer to the temperature of the material at the end of the interval application of power.

The temperature and power applied to the material to be vaporized typically refers to the temperature and power applied to the portion of the material (e.g., the material on the wick in some variations) that will end up reforming into a vapor through the application of the energy, e.g., near the surface, rather than the bulk of the material to be vaporized.

In some embodiments, the temperature and power readings can be gathered only when a user's puff is detected, such as through puff sensor 270. Detection of the user's puff can thus activated the microcontroller to begin calculating the amount of vapor drawn, while detection of the end of the user's puff can cause the microcontroller to stop calculating the amount of vapor drawn. Thus, in some embodiments, equation 1 can be integrated over the duration of a puff. In other embodiments, the measurements can be taken continuously and integrated over the duration of time that the device is on. In yet another embodiment, the integration time period can be pre-set or user selected.

In some embodiments, the TPM can be adjusted to determine the total amount of a particular compound inhaled, such as the total amount of an active ingredient, such as nicotine. For example, the TPM can be multiplied by the percentage of active ingredient in the vaporizable material, as described further below.

Figure 10:
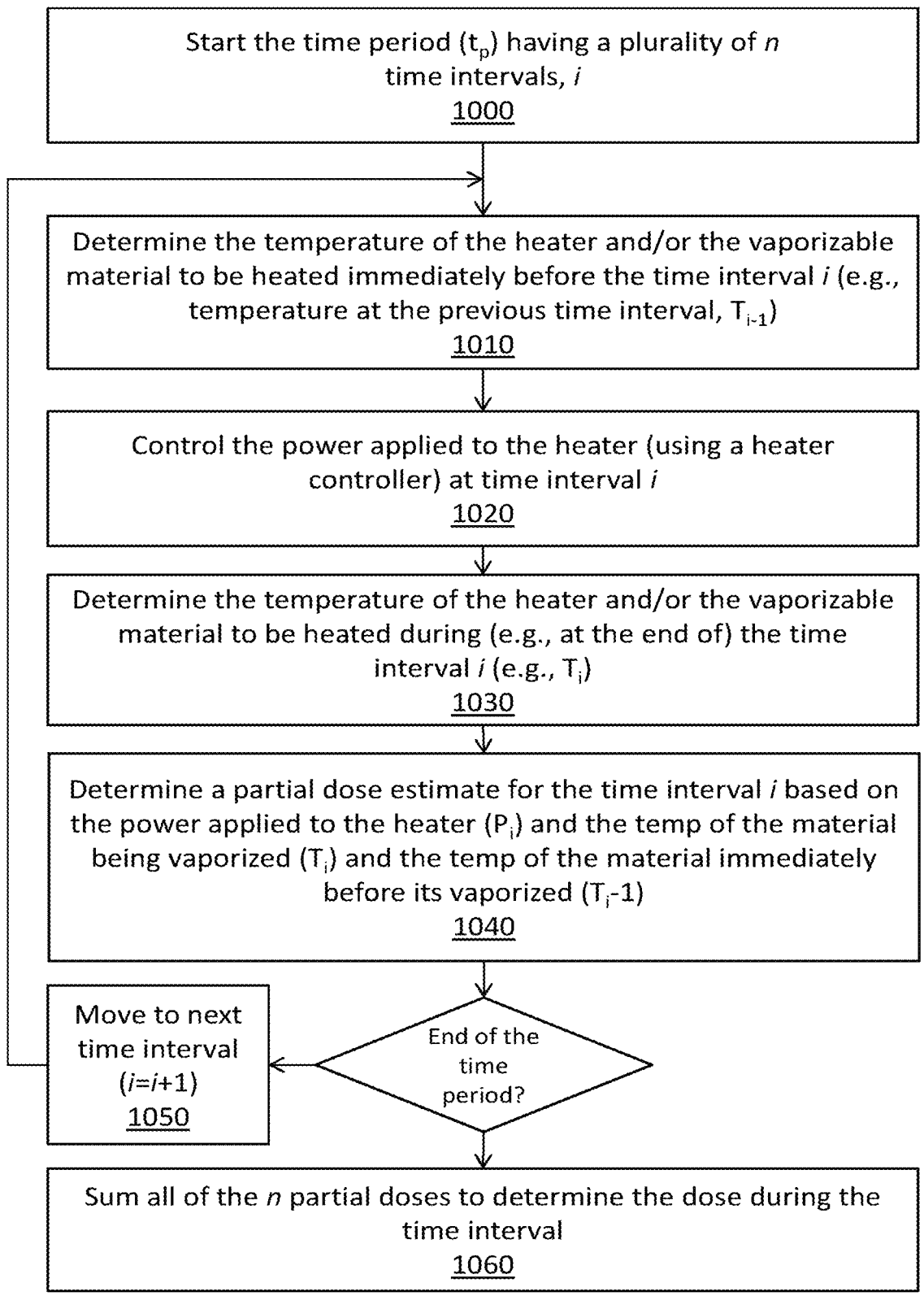
FIG. 10 schematically illustrates one method of determining a dose of vapor over a time interval as described herein.

FIG. 10 illustrates this first method of determining a vapor dose over a time interval as just described. For example, in FIG. 10 the time period for determining the dose ($t_p$) may be initially set or started 1000. The start of the time period may be triggered by the user, physician or other party (e.g., manually) or it may automatically start, e.g., when a user begins puffing on the vaporizer (e.g., using a puff sensor). The duration of the time period may also be predetermined (e.g., fixed, e.g., at 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, 20 sec, 25 sec, 30 sec, 35 sec, 40 sec, 45 sec, 50 sec, 55 sec, 60 sec, 1.5 min, 2 min, 3 min, 4 min, 5 min, 10 min, 12 min, 15 min, 20 min, 30 min, 1 hr, 2 hr, 3 hr, 4 hr, 5 hr, 6 hr, 7 hr, 8 hr, 9 hr, 10 hr, 11 hr, 12 hr, etc.) or it may be variable, including set by the use or it may be determined by sensing the end of a puff. In some variations, the time period is set as the start of a session so that the total dose is determined for the entire session, which may include multiple puffs. In some variations, each puff is considered a time period (e.g., using a puff sensor); the dose may be determined per puff, or it may be aggregated over all of the puffs in a session (where a session may be defined as within a particular time window, e.g., 5 minutes, 10 minutes, 20 minutes, 30 minutes, 1 hour, 2 hours, etc.).

The time period typically includes a number of time intervals i (also referred to herein as partial dose time intervals), which divide the time up in to discrete sample periods for which a partial dose may be calculated. The number of time intervals (n) may be predetermined, when the time period is fixed, or it may be open (e.g., continuously incremented). The duration of the time intervals may be fixed or variable, though they are typically fixed. The duration may be, for example, between about 200 msec and about 10 msec. The time intervals may be immediately adjacent to each other (e.g., in real time), or they may be separated by an off period. The time intervals may generally be considered sequential.

For each time interval, a partial dose of vaporizable material (e.g., vapor, including any active ingredients) may be calculated. This may be controlled and/or performed by a vaporized dose predictor (e.g., VMP unit) portion of the apparatus (or in communication with the apparatus), as described above. During each time increment, i, the apparatus may store the temperature of the heater and/or the vaporizable material near the heater, from the previous time interval, $T_{i-1}$ 1010. This temperature value ($T_{i-1}$) may reflect the temperature of the material to be vaporized during this time interval and may therefore be the temperature at the very start (or just before the very start) of the time interval. During each time interval the apparatus controls the power applied to the heater for that interval (i) 1020. Note that when power is not being applied to heat heater, the power value may be zero; if the heater is still at a different temperature than the previous time increment (i–1), then there may still be vapor produced, if not then little vapor may be produced. The power controller (heater controller) may transmit the power that is causing to be delivered to the heater to the vaporized dose predictor.

The apparatus may also transmit the temperature of the heater and/or the vaporizable material to be vaporized (e.g., the material near the heater) during the time interval ($T_i$) to the vaporized dose predictor 1030.

The system may then determine (e.g., using the vaporized dose predictor) a partial dose estimate for the current time interval, i, using the power applied to the heater and the temperature immediately prior to the interval ($T_{i-1}$) and the temperature during the interval ($T_i$) 1040. For example, either equations 1 or 2, discussed above, may be implemented by the vaporized dose predictor. The partial dose estimate may be stored (e.g., separately as a discrete datum, or added to a cumulative dose for the time period, or both), along with any of the information ($P_i$, $T_i$, etc.). The vaporized dose predictor may include one or more memories (e.g., memory registers) for storing these values (note that the $T_i$ in the current interval may become the $T_{i-1}$ during the next interval.

At the end of each time interval, the apparatus may check to see if the end of the time period has been reached, either because of a predetermined number of intervals (n) has been reached (i=n) or because of some other triggering event (e.g., the end of a puff, end of a session, etc.), or both. If not, then the system may move onto the next interval, incrementing the interval (i=i+1) 1050. Once the end has been reached, in some variations (e.g., where a cumulative register has not been kept), all of the partial doses may be added 1060. Note that in any of these variations, this step of adding all of the partial doses may be done in an ongoing manner, e.g., accumulating them (summing them) as each new interval is passed. Thus, the step of summing the calculated partial doses in the vaporized dose predictor unit to determine a total dose of vapor delivered during the time period may be done either at the end of the time period or it may be done during the duration of the time period, as the partial doses are determined.

EXAMPLES

Figure 2:
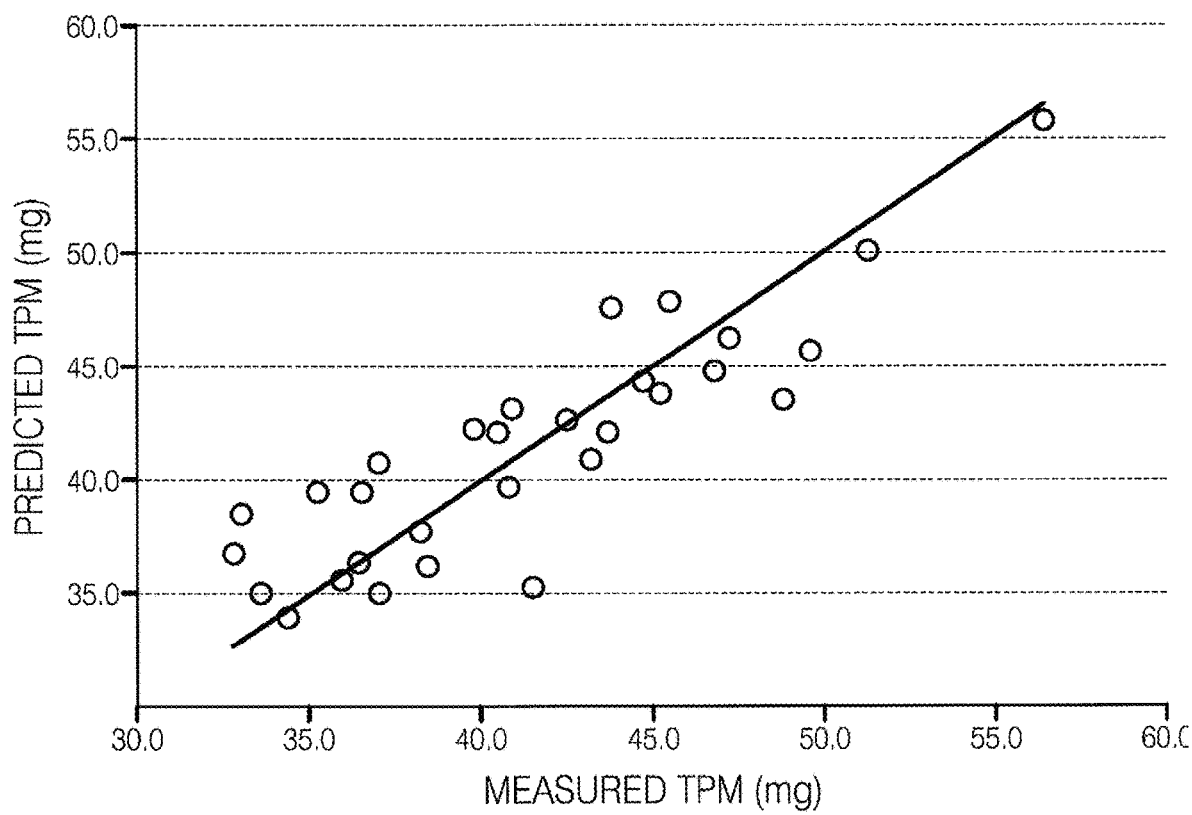
FIG. 2 illustrates the accuracy of the methods and apparatuses for estimating/predicting vapor dosage as described herein, showing a comparison of the dose estimated as described herein (solid line) compared to actual measured dose delivered (circles).

FIGS. 2 and 3 show a relationship of predicted TPM using equation 1 and actual readings of TPM, using an inhalation or smoking machine. The graph of FIG. 2 shows the relationship of predicted TPM (solid line) and measured TPM (dots) for the machine trials. In this trial, the R-squared is 0.78.

To gather the data for FIGS. 2 and 3, an inhalation or smoking machine was set up using an e-vaporizer device loaded with a separate detachable pod holding a vaporizable material. Two devices were arranged in series. Measurement for temperature and power were collected. Ten puffs were taken with the inhalation or smoking machine (at 55 cc/3 sec). The mass loss (or TPM loss) was measured every ten puffs. 31 sample readings were collected using two prototype electronic vaporizer device devices and four prototype pods. The data collected for power and temperature were analyzed. A comparison of the power and temperature data were compared to actual measured mass loss data to correlate the evaporation rate to energy consumption and temperature. It was found that with an $R^2$=0.78, twenty-nine (29) samples fell within ±15% and the remaining two (2) samples fell within ±17%. FIG. 2 shows a graphical relationship of the total particulate mass (TPM), predicted and the measured values. FIG. 3 shows the full data set of predicted values against the actual readings.

In the example shown in FIG. 2, by performing the vaporized mass prediction formula according to equation 1 as described herein, the tabular and graphical relationship of predicted TPM (mg) to actual TPM (mg) can be established. The vaporized mass prediction formula can be utilized to create a program that can be utilized by the VMP unit. The values can be transmitted to the calibrating device through a wireless or wired data transfer, and more preferably can be embedded directly into the vaporizing device itself. The results of the smoking experiment shown in FIG. 2 can provide information to and permit the user, or other individual, to control the amount of vaporizable material correlated to the TPM level.

The results in FIGS. 2 and 3 demonstrate that equation 1 can advantageously improve over inconsistencies that can arrive when function-fitting and/or assuming that the puffing duration and/or power to mass removal can be correlated.

A smoking test by human subjects was also conducted using electronic vaporizer devices configured with separate detachable pods holding vaporizable material. The criteria for the human subjects included a voluntary participation of users, who already smoked or vaped, either regularly or habitually, a diversity in smoking patterns or random puffing habits. Participants were asked to puff normally, and a wide variety of puffing behaviors were observed from subject to subject and even between puffs from the same subject. Thus, participants' puffing attributes were variable and included puffing from 1 to 5 mg per puff; e.g., for some subject's puffs were consistently approximately 3 mg, while others were 2 mg in one puff and 4 mg in the next. The table of FIG. 4 shows the measured TPM for human trials. The first column shows % error from target (which was 40 mg). The second column shows error from mean, which can be a metric for further adjustment of the vaporized mass prediction formula. The formulations of vaporizable materials in the proprietary pods can contain 40 mg of total liquid, which can correspond to 2 mg of nicotine (5% nicotine by mass). The test shows that calibration of the device can accurately portion a dose that can be of a specific metered dose. Here, the smoking test was run with eleven human subjects. The twenty-three sample readings (or results) fall within ±15% of the 40 mg target. The other two samples are within ±17%. The mean of the samples taken is 42.1 mg. Coefficient of variance is 5.96%. All samples fall within ±11% of the mean.

Figure 5:
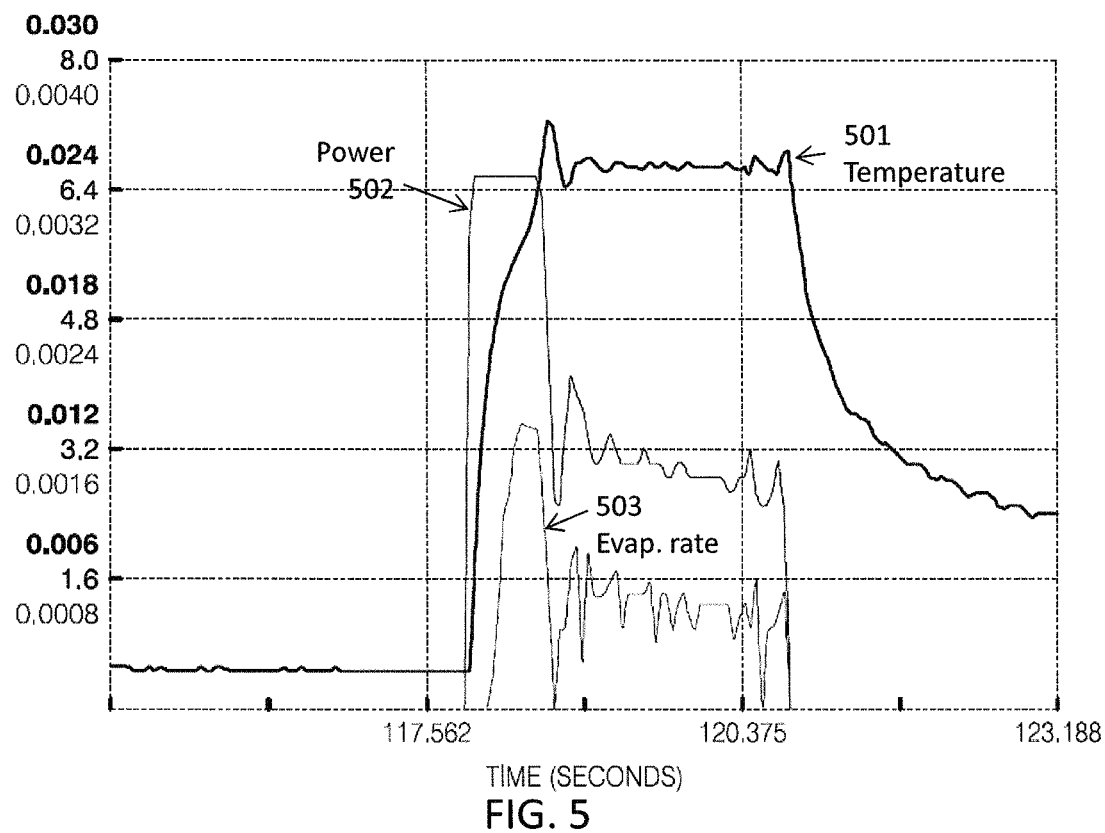
FIGS. 5 and 6 graphically illustrate the relationship between applied power at a vaporizer heater, temperature of the heater, and an estimated evaporation rate (dose) at a 35 cc and 70 cc control "puff", respectively.
Figure 6:
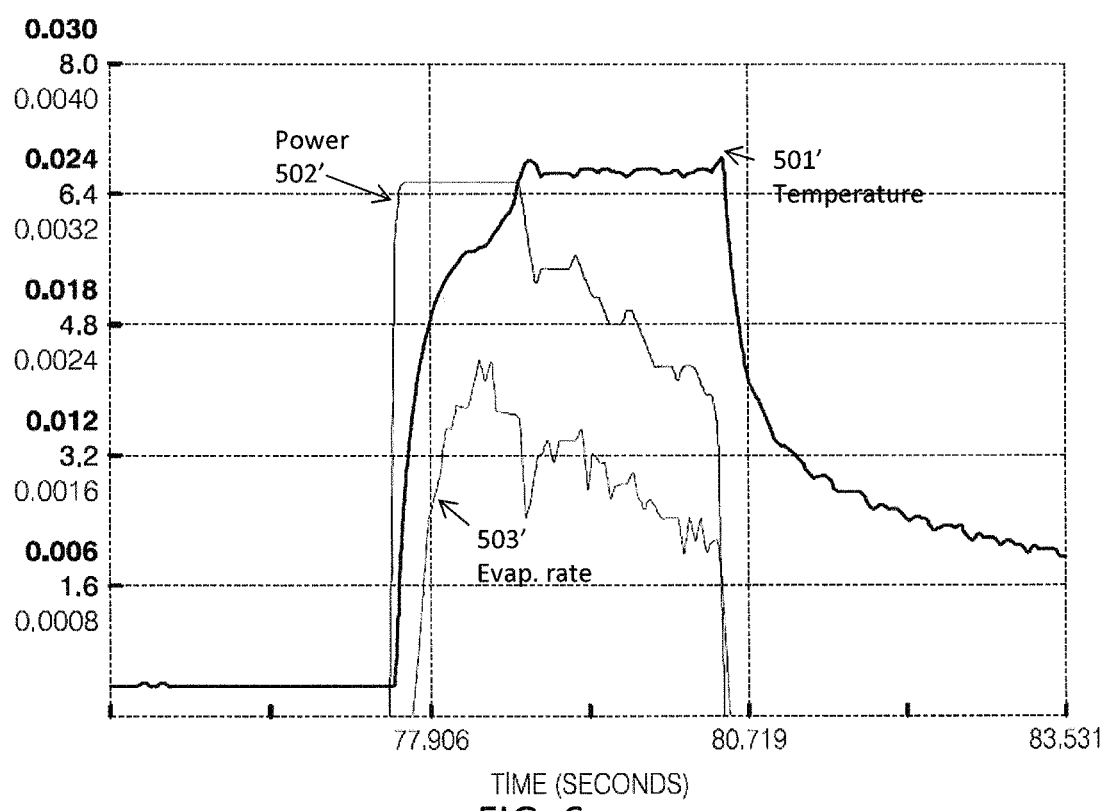

In some embodiments, merely measuring a puff duration can result in inaccurate quantitation of a vaporized mass. FIG. 5 and FIG. 6 show graphs that correlate TPM, as a function of power, time and temperature. In performing the vaporized mass prediction method as described herein, where upon a relationship of TPM (mg) as a function of power, time and temperature can be established.

In an aspect, in FIG. 5 and FIG. 6, the present disclosure illustrates the real-time graph program capturing mass vaporized (mg) as a function of power, time and temperature. In FIG. 5 and FIG. 6, the thickest line 501, 501' (labeled temperature) is given by the resistance ratio that ($R_{heater}/R_{reference}$) that is proportional to the temperature of the heater (show subtracted from 1); this may multiplied by 1/TCR to convert to units (e.g., ° C.), for example. Thus, in calculating the dose, the temperature ($T_i$ and $T_{i-1}$) determined for each interval is the measured resistance of the coil and baseline is a baseline resistance (established separate from the heater, presumably at room temperature). The temperature rise is linear with temperature rise above room temperature by a factor of 1/TCR, where TCR is the temperature coefficient of resistance. In both FIG. 5 and FIG. 6, the line of medium thickness 502, 502' (labeled power) is power delivered to the coil (e.g., in watts). Further, in both FIG. 5 and FIG. 6, the thinnest line 503, 503' (labeled evaporation rate) is evaporation (vaporization) rate, in this example in mg/msec. This may be derived by implementing a formula such as expressed in equation 1 or equation 2, previously discussed. The values in this example may be divided by 50 ms/sample (the interval time) to arrive at mg/msec instead of mg/sample. This curve can be integrated over the time course of the puff to give the total dose delivered from a puff. In FIG. 5 and FIG. 6, the axes on the left are scaled differently for the power, temperature and evaporation rates. FIG. 5 and FIG. 6 illustrate examples of puffs taken at two different predetermined puff profiles. In FIG. 5, a 35 cc puff was pulled over about 3 seconds. In FIG. 6, a 70 cc puff over about 3 seconds, where the flow rate in FIG. 6 is twice that in FIG. 5. Illustratively, comparing FIG. 6 to FIG. 5, there is a higher mass removal (mass vaporized) for the faster puff of FIG. 6. Different puffs vaporize differing amounts of material. The present disclosure presents that the system is responsive to varying puff profiles, which do not typically have a uniform flow rate during the puff, and the duration may vary. This behavior can be further supported by the human study that is discussed above, where consistent results were obtained, even with variances in puffing attributes representative of individual or unique human puffs.

Calculation of Vaporizable Material Vaporized—Second Exemplary Method

In some embodiments, a vaporizing device, such as device 100, can be calibrated based on a previous measurement performed using a same or similar device such that an amount of vaporized material can be determined based upon the performance of the same or similar device. For example, the device can be calibrated through a function fit method to determine a relationship between total particulate matter (TPM) release content (mg) and one or more vaporization parameters of aerosolizing materials from the device by a function fit method.

In some cases, the method for calibration of the device to obtain active material content from the relationship of total particulate matter (TPM) release content (mg) to vaporization parameters of aerosolizing materials can comprise setting up an analytical inhalation or smoking machine to its functioning operating parameters and testing the device under one or more conditions. In some cases, conditions that can be varied can comprise puff volume and/or flow rate. The conditions (e.g., vaporization parameters) can include one or more variable chosen from the group consisting of puff duration (sec), puff volume (ml), flow rate (ml/sec), power (watts), voltage (volts). In some cases, exemplary ranges include, but are not limited to 1 mL-100 mL volume; 0.2 s-10 s duration; 2-100 mL/s; 2.5-4.2V, respectively.

Total particulate matter (TPM) can be collected from the electronic vaporizer device. In some cases, the TPM can be collected on a filter pad. The filter pad can be weighed before and after TPM is collected on the filter such that the weight of the TPM on the filter can be determined. In some cases, the weight of the filter can be tared. The weight of the material in the device to be vaporized can be recorded prior to vaporization. In some cases, the weight of the vaporizable material in the device can be measured and recorded prior to operating the device. The weight of the vaporizable material in the device can be measured and recorded after one or more puffs on the device. A difference in weight of the vaporizable material between the initial weight and the weight after one or more puffs can be compared to a weight of TPM collected on the filter. In some cases, the difference in weight of the vaporizable material between the initial weight and the weight after one or more puffs and the weight of TPM collected on the filter can be substantially the same. The TPM collected on the filter can comprise material vaporized from the vaporizable material in the device during the one or more puffs.

In some cases, an analytical inhalation or smoking device can be a machine configured to simulate inhalation of a vaporized material from a vaporizing device by a human. While the machine smoking device vaporizes the formulation in the one or more devices, TPM from the device can be collected onto one or more filter pads. Each device can have TPM released from the electronic vaporizer device collected on a different filter pad. For each filter pad the amount of TPM released by a device can be determined. The amount of TPM released by an individual device relative to the initial weight of vaporizable material can be calculated. In some cases, this procedure can be repeated with variable inhalation conditions, for example, with progressively increasing and/or decreasing puff duration (sec) of the machine inhalation or smoking device. In some cases, the procedure can be repeated with varying puff volume (ml) of the machine smoking device. The puff volume can vary in the range of 1 mL-100 mL, more preferably, 20-80 mL, most preferably 30-60 mL. In some cases, the procedure can be repeated with varying flow rate of the machine smoking device. Flow rate of the machine inhalation or smoking device can vary in a range of 2-100 mL/s, more preferably, 5-50 mL/s, most preferably 10-30 mL/s. In some cases, the procedure can be repeated with varying power of the machine inhalation or smoking device. Power (watts) of the smoking device can vary in the range of 2 watts to 20 watts, more preferably 3 watts to 8 watts. In some cases, the procedure can be repeated with varying voltage of the machine inhalation or smoking device. Voltage of the device can vary in a range of 2.5-4.2V, more preferably 3.0-4.2V.

Figures 9A, 9B:
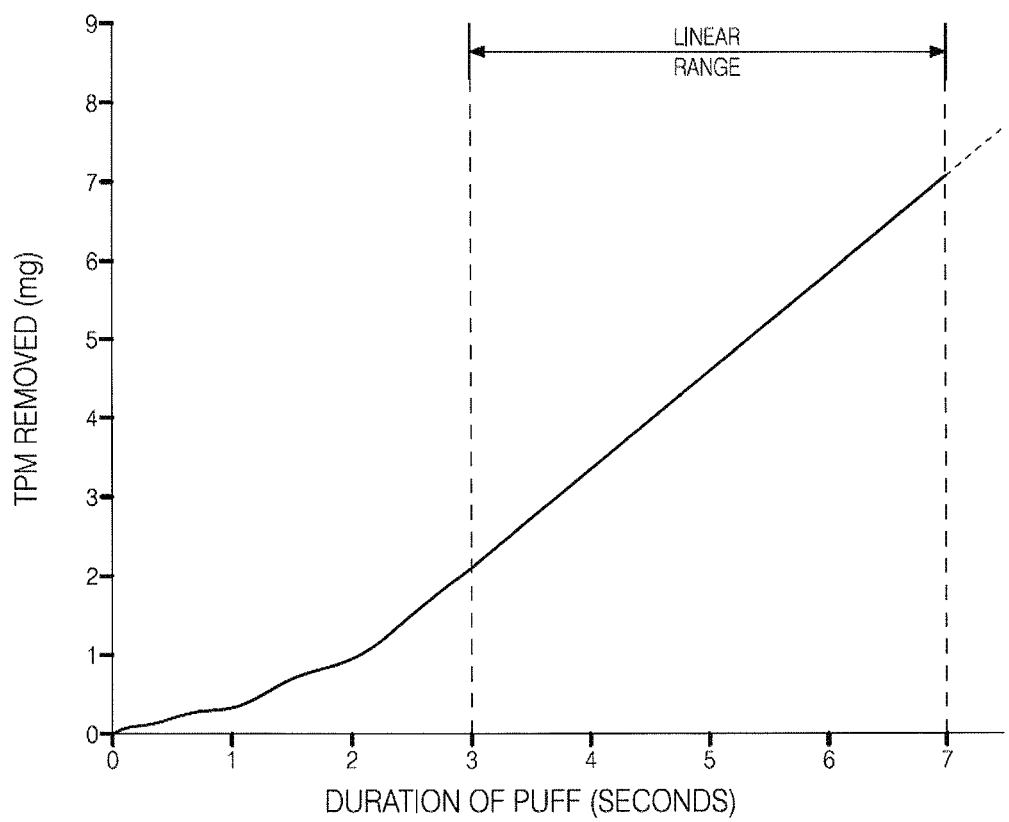
FIG. 9A is a table illustrating one variation of a look-up table that can be used to estimate the amount of vapor inhaled by a user based upon calibration data.
FIG. 9B graphically illustrates data such as that shown in FIG. 9A, which may be used to estimate the amount of vapor inhaled by a user.

The puff volumes to the corresponding TPM release content (mg) can be tabulated. A relationship between puff volume and corresponding TPM release content (mg) can be displayed graphically and/or in a table and can be used to predict, determine, or estimate the amount of vapor consumed by the user when using a device. For example, FIGS. 9A and 9B show an exemplary look-up table and graph that can be used to determine or estimate the amount of vapor inhaled by a user based upon calibration data previously gathered from an inhalation or smoking machine. The values can be transmitted to the device, such as the microcontroller within the PCB 240 of device 100, through a wireless or wired data transfer. The results of the calibration experiment shown in FIGS. 9A and 9B can provide information to and permit the user, or other individual, to understand or control the amount of active material correlated to the TPM level.

Vaporized Mass Predictor Unit

A vaporizer device, such as devices 10, 100, 100', may include a vaporized mass predictor (e.g., VMP unit), such as within the control unit 10, 110. The VMP 109 may execute the logic described herein to determine the dose delivered according to any of the methods described herein. In certain embodiments, the VMP is communicatively coupled to one or more of: a puff sensor (optional), a heater (e.g., heating element) controller, an alert unit and/or controlling logic. In certain embodiments, a VMP unit is communicatively coupled to a puff sensor, timer, heater controller and either the alert unit or controlling logic. In certain embodiments, the VMP includes software (e.g., a software module or control logic) that runs on the processor. The VMP unit may integrate power readings from the heater controller, temperature readings from the temperature sensor; and in some cases puff duration or puff frequency readings from the puff sensor and timer. The VMP unit will then calculate how much vapor has been vaporized from a vaporizable material.

In some embodiments, the VPM unit of each device can be calibrated separately. In some embodiments, a VPM calibration can be set based upon a known vaporization material. In some embodiments, the device can include a user interface that allows the user to input the material being vaporized, which in turn sets the constants a, b, c for equation 1 and/or the function fit curve or look-up table.

In some embodiments, the VMP (or another component of the control unit) can calculate the active material content based upon the TPM. The TPM to active material content can be correlated based on the composition of the organic materials loaded into the electronic vaporizer device. For example, for an organic material, that contains a percentage of 20-25% active material, would correlate to a TPM, mg, containing said percentage of active material. In some cases, it may be reasonable to assume total conversion (aerosolization) of the active material. For example, for organic material selected from *Cannabis* extract, where the organic material is a *Cannabis* extract containing 25% cannabidiol (CBD), then the TPM, mg, correlated to said 25% CBD, means the TPM, mg has the percentage of said active compound, preferably assuming total conversion (aerosolization) of the active material.

In certain embodiments, the VMP unit is adjustable by the user, and allows the user to preset an amount of vaporizable material to be vaporized before the user is alerted, or elements of the vaporizer device are disabled, or the controlling logic is implemented. In certain embodiments, the VMP unit will then engage an alert unit that alerts a user when a preset amount of a vaporizable material is vaporized. In certain embodiments, the VMP unit will then disable the vaporizer device when a preset amount of a vaporizable material is vaporized. In certain embodiments, the VMP is user adjustable, so that the vaporizer device will vaporize a target amount of material in a single puff.

In certain embodiments, the VMP is user adjustable, so that the vaporizer device will vaporize a target amount of material in a plurality of puffs. In certain embodiments, the VMP is user adjustable, so that the vaporizer device will vaporize a target amount of material in a single puff. In some variations, the VMP is user adjustable so that the device can be disable for a period of time after the target amount of material has been vaporized. The VMP may be user adjustable so that the device can engage an alert after a target amount of material has been vaporized. In certain embodiments, the VMP engages an alert when the amount of vaporizable material in the vaporizer device falls below a preset threshold. In certain embodiments, the VMP unit is communicatively coupled to a memory unit and stores a plurality of any of the following measurements: power, temperature, puff duration readings, or any combination thereof. In certain embodiments, the VMP unit will calculate a cumulative amount of vaporizable material that is vaporized. If for example a user does not fully vaporize the preset limit in one puff the VMP unit will keep track of the amount of vaporizable material vaporized over a plurality of puffs. In certain embodiments, the VMP unit is a software module. In certain embodiments, the VMP unit is a microprocessor.

In certain embodiments, the VMP unit will generate a puff profile that tracks power, temperature, pressure or a combination thereof over time.

In certain embodiments, the accuracy of the measured TPM vaporized from a VMP unit is at least ±25% of a predicted value. In certain embodiments, the accuracy of the measured TPM vaporized from a VMP unit is at least ±20% of a predicted value. In certain embodiments, the accuracy of the measured TPM vaporized from a VMP unit is at least ±15% of a predicted value. In certain embodiments, the accuracy of the measured TPM vaporized from a VMP unit is at least ±10% of a predicted value. In certain embodiments, the accuracy of the measured TPM vaporized from a VMP unit is at least ±5% of a predicted value. In certain embodiments, the VMP unit is a software component associated with the processor.

In certain embodiments, the preset amount of vaporized material allowed before the VMP unit engages an alert is adjustable. In certain embodiments, the preset amount of vaporized material allowed before the VMP unit engages the controlling logic is adjustable. Adjustment allows a user to be alerted when a certain amount of vaporizable material has been vaporized, and inhaled by the user, this allows for an improved user experience by precise control in dosage of a vaporizable material (e.g., nicotine, cannabinoid). In certain embodiments, a user can preset an amount of vaporizable material vaporized in mg of TPM. In certain embodiments, the preset amount of vaporizable material vaporized in mg of TPM is between about 1 mg and about 1000 mg. In certain embodiments, the preset amount of vaporizable material vaporized in mg of TPM is between about 1 mg and about 100 mg. In certain embodiments, the preset amount of vaporizable material vaporized in mg of TPM is between about 10 mg and about 100 mg. In certain embodiments, the preset amount of vaporizable material vaporized in mg of TPM is between about 10 mg and about 1000 mg. In certain embodiments, the preset amount of vaporizable material vaporized in mg of TPM is between about 1 mg and about 50 mg. In certain embodiments, the preset amount of vaporizable material vaporized in mg of TPM is between about 1 mg and about 25 mg. In certain embodiments, the preset amount of vaporizable material vaporized in mg of TPM is less than about 1 mg. In certain embodiments, the preset amount of vaporizable material vaporized in mg of TPM is about 1 mg. In certain embodiments, the preset amount of vaporizable material vaporized in mg of TPM is about 2 mg. In certain embodiments, the preset amount of vaporizable material vaporized in mg of TPM is about 3 mg. In certain embodiments, the preset amount of vaporizable material vaporized in mg of TPM is about 4 mg. In certain embodiments, the preset amount of vaporizable material vaporized in mg of TPM is about 5 mg. In certain embodiments, the preset amount of vaporizable material vaporized in mg of TPM is about 6 mg. In certain embodiments, the preset amount of vaporizable material vaporized in mg of TPM is about 7 mg. In certain embodiments, the preset amount of vaporizable material vaporized in mg of TPM is about 8 mg. In certain embodiments, the preset amount of vaporizable material vaporized in mg of TPM is about 9 mg. In certain embodiments, the preset amount of vaporizable material vaporized in mg of TPM is about 10 mg. In certain embodiments, the preset amount of vaporizable material vaporized in mg of TPM is about 20 mg. In certain embodiments, the preset amount of vaporizable material vaporized in mg of TPM is about 30 mg. In certain embodiments, the preset amount of vaporizable material vaporized in mg of TPM is about 40 mg. In certain embodiments, the preset amount of vaporizable material vaporized in mg of TPM is about 50 mg. In certain embodiments, the preset amount of vaporizable material vaporized in mg of TPM is about 60 mg. In certain embodiments, the preset amount of vaporizable material vaporized in mg of TPM is about 70 mg. In certain embodiments, the preset amount of vaporizable material vaporized in mg of TPM is about 80 mg. In certain embodiments, the preset amount of vaporizable material vaporized in mg of TPM is about 90 mg. In certain embodiments, the preset amount of vaporizable material vaporized in mg of TPM is about 100 mg.

In certain embodiments, a user can preset an amount of vaporizable material vaporized in mg of an active ingredient (e.g., nicotine, cannabinoid, THC). In certain embodiments, the preset amount of vaporizable material vaporized in mg of an active ingredient is between about 1 mg and about 1000 mg. In certain embodiments, the preset amount of vaporizable material vaporized in mg of an active ingredient is between about 1 mg and about 100 mg. In certain embodiments, the preset amount of vaporizable material vaporized in mg of an active ingredient is about 0.05 mg. In certain embodiments, the preset amount of vaporizable material vaporized in mg of an active ingredient is about 0.1 mg. In certain embodiments, the preset amount of vaporizable material vaporized in mg of an active ingredient is about 0.2 mg. In certain embodiments, the preset amount of vaporizable material vaporized in mg of an active ingredient is about 0.3 mg. In certain embodiments, the preset amount of vaporizable material vaporized in mg of an active ingredient is about 0.4 mg. In certain embodiments, the preset amount of vaporizable material vaporized in mg of an active ingredient is about 0.5 mg. In certain embodiments, the preset amount of vaporizable material vaporized in mg of an active ingredient is about 0.6 mg. In certain embodiments, the amount of vaporizable material vaporized in mg of an active ingredient is about 0.7 mg. In certain embodiments, the preset amount of vaporizable material vaporized in mg of an active ingredient is about 0.8 mg. In certain embodiments, the preset amount of vaporizable material vaporized in mg of an active ingredient is about 0.9 mg. In certain embodiments, the preset amount of vaporizable material vaporized in mg of an active ingredient is about 1 mg. In certain embodiments, the preset amount of vaporizable material vaporized in mg of an active ingredient is about 2 mg. In certain embodiments, the preset amount of vaporizable material vaporized in mg of an active ingredient is about 3 mg. In certain embodiments, the preset amount of vaporizable material vaporized in mg of an active ingredient is about 4 mg. In certain embodiments, the preset amount of vaporizable material vaporized in mg of an active ingredient is about 5 mg. In certain embodiments, the preset amount of vaporizable material vaporized in mg of an active ingredient is about 6 mg. In certain embodiments, the preset amount of vaporizable material vaporized in mg of an active ingredient is about 7 mg. In certain embodiments, the preset amount of vaporizable material vaporized in mg of an active ingredient is about 8 mg. In certain embodiments, the preset amount of vaporizable material vaporized in mg of an active ingredient is about 9 mg. In certain embodiments, the preset amount of vaporizable material vaporized in mg of an active ingredient is about 10 mg. In certain embodiments, the preset amount of vaporizable material vaporized in mg of an active ingredient is about 10 mg. In certain embodiments, the preset amount of vaporizable material vaporized in mg of an active ingredient is about 20 mg. In certain embodiments, the preset amount of vaporizable material vaporized in mg of an active ingredient is about 30 mg. In certain embodiments, the preset amount of vaporizable material vaporized in mg of an active ingredient is about 40 mg. In certain embodiments, the preset amount of vaporizable material vaporized in mg of an active ingredient is about 50 mg. In certain embodiments, the preset amount of vaporizable material vaporized in mg of an active ingredient is about 60 mg. In certain embodiments, the preset amount of vaporizable material vaporized in mg of an active ingredient is about 70 mg. In certain embodiments, the preset amount of vaporizable material vaporized in mg of an active ingredient is about 80 mg. In certain embodiments, the preset amount of vaporizable material vaporized in mg of an active ingredient is about 90 mg. In certain embodiments, the preset amount of vaporizable material vaporized in mg of an active ingredient is about 100 mg.

In a certain embodiment, the VMP unit is user adjustable using a button. In a certain embodiment, the VMP unit is user adjustable using a dial. In a certain embodiment, the VMP unit is user adjustable using a capacitive interface. In a certain embodiment, the VMP unit is user adjustable using a wireless connection. In a certain embodiment, the VMP unit is user adjustable using voice communication.

In a certain embodiment, the type of vaporizable material is adjustable. In a certain embodiment the type of vaporizable material that is adjustable is nicotine. In a certain embodiment, the type of vaporizable material that is adjustable is a *Cannabis*. In a certain embodiment, the type of vaporizable material that is adjustable is a cannabinoid. In a certain embodiment, the type of vaporizable material that is adjustable is a medicinal compound. In a certain embodiment, the type of vaporizable material that is adjustable is a botanical. In a certain embodiment, the type of vaporizable material that is adjustable is a nutraceutical. In some embodiments, the type of material that is adjustable is formulation specific (e.g., a percent compound dissolved in a specific solvent).

In a certain embodiment, the VMP unit integrates readings from the puff sensor, temperature sensor, heating element controller and timer to create profiles of the readings. A power profile is the change in power delivery over time. A temperature profile is the change in temperature over time. In a certain embodiment, the profile is measured from the initiation of the puff, as measured by the puff sensor to the cessation of the puff, as measured by the puff sensor. In a certain embodiment, the VMP unit stores a plurality of profiles in a memory unit.

In real time, the VMP unit can take a device's data and use it to calculate cumulative TPM in mg. For example, when the TPM reaches 40 mg, the human subject can be prompted to stop puffing, or the heating element can be adjusted or turned off. The constants can be modified to account for different pods and different liquids.

In certain embodiments, the electronic vaporizer device utilizing the method of determining the amount of vapor delivered to the user described herein, such as device 100, comprises an alert unit. In certain embodiments, the alert unit alerts a user when a preset amount of vaporizable material is vaporized. In certain embodiments, the alert unit notifies the user when the vaporizer device is low on vaporizable material. In certain embodiments, the alert unit alerts the user when the amount of vaporizable material in the vaporizer device falls below 10%. In certain embodiments, the alert unit alerts the user when the amount of vaporizable material in the vaporizer device falls below 5%. In certain embodiments, the alert unit is a light emitting diode (LED). In certain embodiments, the alert unit is an organic light emitting diode (OLED). In certain embodiments, the LED or OLED is communicatively coupled to the VMP unit. In certain embodiments, the LED or OLED illuminates when the amount of vapor delivered to a user meets or exceeds a preset amount. In certain embodiments, the LED or OLED flashes when the amount of vapor delivered to a user meets or exceeds a preset amount. In certain embodiments, the LED or OLED emits light in different color spectrums. In certain embodiments, the LED or OLED emits red light. In certain embodiments, the LED or OLED emits orange light. In certain embodiments, the LED or OLED emits yellow light. In certain embodiments, the LED or OLED emits green light. In certain embodiments, the LED or OLED emits blue light. In certain embodiments, the LED or OLED emits purple light. In certain embodiments, the LED or OLED emits more than one color light, the more than one color can be any combination of the above mentioned colors. In certain embodiments, the LED or OLED emits flashing light in any of the aforementioned colors.

In certain embodiments, the electronic vaporizer device utilizing the method comprises an alert unit. In certain embodiments, the alert unit is a piezoelectric speaker. In certain embodiments, the piezoelectric speaker is communicatively coupled to the VMP unit. In certain embodiments, the piezoelectric speaker emits sound when the amount of vapor delivered to a user meets or exceeds a preset amount. In certain embodiments, the sound is a chime, bell, tone, multitoned sound, song or the like.

In certain embodiments, the electronic vaporizer device utilizing the method comprises an alert unit. In certain embodiments, the alert unit is a vibration motor, which provides tactile feedback to the user. In certain embodiments, the vibration motor is communicatively coupled to the VMP unit. In certain embodiments, the vibration motor activates when the amount of vapor delivered to a user meets or exceeds a preset amount.

In certain embodiments, the electronic vaporizer device utilizing the method comprises more than one alert unit. In certain embodiments, the more than one alert unit is an LED or OLED, a piezoelectric speaker, vibration motor or any combination thereof.

The alert unit (or simply the alert) may be configured as a dose output, as shown schematically in FIG. 1. The dose output may be a visual output (e.g., LCD/LED, etc.) and/or a wireless output to a display device (e.g., a smartphone or other wearable device running an application that communicates with the vaporization device, typically wirelessly). The application and therefore the hardware (e.g., wearable device, remote server, etc.) running the application may store, analyze, transmit, display and/or aggregate the dose information (and/or the raw timing, temperature and power, etc., data).

In certain embodiments, the electronic vaporizer device utilizing the method of determining the amount of vapor delivered to the user described herein, such as device 100, includes a controlling logic or a disabling unit. In certain embodiments, the controlling logic is a software module. In certain embodiments, the controlling logic is a firmware module. In certain embodiments, the controlling logic is a hardware element. In certain embodiments, the controlling logic will prompt the VMP unit to relay instructions to the heating element controller to allow a user to vaporize a target amount of TPM in a single puff. In certain embodiments, the controlling logic will prompt the VMP unit to relay instructions to the heating element controller to allow a user to vaporize a target amount of TPM in a plurality of puffs. In certain embodiments, the controlling logic is communicatively coupled to VMP unit. In certain embodiments, the controlling logic inactivates the heating element. In certain embodiments, the controlling logic modifies the amount of power delivered to the heating element. In certain embodiments, the controlling logic turns the electronic vaporizer device off. In certain embodiments, the user can override the controlling logic to restore proper operation of the vaporizer device.

In any of the apparatuses described herein, the electronic vaporizer device utilizing the method of determining the amount of vapor produced (and therefore delivered to a user), such as devices 10, 100. 100', may include a memory. In certain embodiments, the memory (e.g., memory unit) is hardware that is communicatively coupled to the VMP. In certain embodiments, the memory is internal to the electronic vaporizer device. In certain embodiments, the memory is external to the electronic vaporizer device. In certain embodiments, the memory is configured to store a plurality of any of temperature, power, pressure, time, puff duration, puff frequency measurements and combinations thereof. In certain embodiments, the memory unit is a solid state memory. In certain embodiments, the memory unit is a hard disk.

In any of the electronic vaporizer device described herein, such as devices 10, 100. 100', the apparatus may include a processor. In certain embodiments, the processor may include software, firmware and/or hardware that executes the controlling logic of the device. In certain embodiments, the processor is communicatively coupled to the VMP unit. In certain embodiments, the VMP unit and the processor are the same element. In certain embodiments, the processor is communicatively coupled to the user interface. In certain embodiments, the processor is communicatively coupled to the memory unit.

As described above, the electronic vaporizer devices described herein may include a power source, such as power source 230. In certain embodiments, the power source is removable. In certain embodiments, the power source is a battery. In certain embodiments, the power source is a rechargeable battery. In certain embodiments, the rechargeable battery is a lithium ion battery. In certain embodiments, the rechargeable battery is compatible with a USB charging cable. In certain embodiments, the electronic vaporizer device with a rechargeable battery is compatible with a micro USB charging cable. In certain embodiments, the rechargeable battery is compatible with a charging cradle. A charging cradle is any physical device capable of supporting the electronic vaporizer device while charging; the cradle can either be integral to the electronic vaporizer device, or separate from the electronic vaporizer device. In certain embodiments, the charging cradle has charging contacts, configured to mate to contacts on the electronic vaporizer device. In certain embodiments, the charging cradle charges the electronic vaporizer device using induction technology. In certain embodiments, the charging cradle is an induction charging mat.

The power source may be configured to deliver power to the heating element, and may be regulated by the heater controller. The heater controller may therefore receive charge/power level input from the power source and may adjust its output accordingly. In certain embodiments, the power source is configured to deliver an adjustable amount of power. In certain embodiments, the amount of power is adjustable by the user. In certain embodiments, the amount of power is adjusted by the VMP unit. As mentioned, the power source may be communicatively coupled to the heater controller. In certain embodiments, the power source is configured to deliver an adjustable amount of power and is controlled by the VMP unit. In certain embodiments, the power source delivers between 1 and 100 watts of power. In certain embodiments, the power source delivers between 1 and 50 watts of power. In certain embodiments, the power source delivers between 1 and 20 watts of power. In certain embodiments, the power source delivers between 1 and 10 watts of power. In certain embodiments, the power source delivers between 1 and 8 watts of power. In certain embodiments, the power source delivers between 2 and 10 watts of power. In certain embodiments, the power source delivers between 10 and 100 watts of power. In certain embodiments, the power source delivers between 10 and 50 watts of power. In certain embodiments, the power source delivers between 10 and 20 watts of power. In certain embodiments, the power source delivers about 4 watts of power. In certain embodiments, the power source delivers about 4.5 watts of power. In certain embodiments, the power source delivers about 5 watts of power. In certain embodiments, the power source delivers about 5.5 watts of power. In certain embodiments, the power source delivers about 6 watts of power. In certain embodiments, the power source delivers about 6.5 watts of power. In certain embodiments, the power source delivers about 7 watts of power. In certain embodiments, the power source delivers about 7.5 watts of power. In certain embodiments, the power source delivers about 8 watts of power. In certain embodiments, the power source delivers about 8.5 watts of power. In certain embodiments, the power source delivers about 9 watts of power. In certain embodiments, the power source delivers about 10 watts of power. In certain embodiments, the power source delivers about 20 watts of power. In certain embodiments, the power source delivers about 30 watts of power. In certain embodiments, the power source delivers about 40 watts of power. In certain embodiments, the power source delivers about 10 watts of power. In certain embodiments, the power source delivers about 50 watts of power. In certain embodiments, the power source delivers about 60 watts of power. In certain embodiments, the power source delivers about 70 watts of power. In certain embodiments, the power source delivers about 80 watts of power. In certain embodiments, the power source delivers about 90 watts of power. In certain embodiments, the power source delivers about 100 watts of power. The power applied may alternatively or additionally (and equivalently) be expressed in joules. For example, in certain embodiments, the power source delivers between 1 and 1000 joules to the heater. In certain embodiments, the power source delivers between 1 and 500 joules to the heater. In certain embodiments, the power source delivers between 1 and 100 joules to the heater. In certain embodiments, the power source delivers between 1 and 50 joules to the heater. In certain embodiments, the power source delivers between 1 and 25 joules to the heater. In certain embodiments, the power source delivers between 5 and 25 joules to the heater. In certain embodiments, the power source delivers between 1 and 20 joules to the heater. In certain embodiments, the power source delivers between 5 and 20 joules to the heater. In certain embodiments, the power source delivers between 10 and 500 joules to the heater. In certain embodiments, the power source delivers between 10 and 100 joules to the heater. In certain embodiments, the power source delivers between 10 and 50 joules to the heater. In certain embodiments, the power source delivers between 10 and 20 joules to the heater.

As described above, any of the vaporizer apparatuses described herein may include a heater (heating element). In certain embodiments, the heater is a resistive heating element. In certain embodiments, the heating element forms a coil. In certain embodiments, the coil is wrapped around a wick. In certain embodiments, the wick is in contact with a vaporizable material. In certain embodiments, the wick projects into the vaporizable material.

In certain embodiments, the heating element heats the vaporizable material to between 40 and 1000 degrees Celsius. In certain embodiments, the heating element heats the vaporizable material to between 100 and 900 degrees Celsius. In certain embodiments, the heating element heats the vaporizable material to between 100 and 800 degrees Celsius. In certain embodiments, the heating element heats the vaporizable material to between 100 and 700 degrees Celsius. In certain embodiments, the heating element heats the vaporizable material to between 100 and 600 degrees Celsius. In certain embodiments, the heating element heats the vaporizable material to between 100 and 500 degrees Celsius. In certain embodiments, the heating element heats the vaporizable material to between 100 and 400 degrees Celsius. In certain embodiments, the heating element heats the vaporizable material to between 100 and 300 degrees Celsius. In certain embodiments, the heating element heats the vaporizable material to between 180 and 250 degrees Celsius. In certain embodiments, the heating element heats the vaporizable material to between 100 degrees Celsius and 200 degrees Celsius. In certain embodiments, the heating element heats the vaporizable material to between 125 degrees Celsius and 175 degrees Celsius. In certain embodiments, the heating element heats the vaporizable material to about 150 degrees Celsius. In certain embodiments, the heating element heats the vaporizable material to between 200 and 300 degrees Celsius. In certain embodiments, the heating element heats the vaporizable material to between 225 and 275 degrees Celsius. In certain embodiments, the heating element heats the vaporizable material to about 250 degrees Celsius. In certain embodiments, the heating element heats the vaporizable material to between 300 and 400 degrees Celsius. In certain embodiments, the heating element heats the vaporizable material to between 325 and 375 degrees Celsius. In certain embodiments, the heating element heats the vaporizable material to about 350 degrees Celsius. In certain embodiments, the heating element heats the vaporizable material to between 400 and 500 degrees Celsius. In certain embodiments, the heating element heats the vaporizable material to between 500 and 600 degrees Celsius. In certain embodiments, the heating element heats the vaporizable material to between 600 and 700 degrees Celsius. In certain embodiments, the heating element heats the vaporizable material to between 700 and 800 degrees Celsius. In certain embodiments, the heating element heats the vaporizable material to between 800 and 900 degrees Celsius. In certain embodiments, the heating element heats the vaporizable material to between 900 and 1000 degrees Celsius. In certain embodiments, when the vaporizable material is *Cannabis* or a cannabinoid, the heating element heats the vaporizable material to between 300 and 400 degrees Celsius. In certain embodiments, when the vaporizable material is *Cannabis* or a cannabinoid, the heating element heats the vaporizable material to between 325 and 375 degrees Celsius. In certain embodiments, when the vaporizable material is *Cannabis* or a cannabinoid, the heating element heats the vaporizable material to about 350 degrees Celsius. In certain embodiments, when the vaporizable material is nicotine or a nicotine derivative, the heating element heats the vaporizable material to between 200 and 300 degrees Celsius. In certain embodiments, when the vaporizable material is nicotine or a nicotine derivative, the heating element heats the vaporizable material to between 225 and 275 degrees Celsius. In certain embodiments, when the vaporizable material is nicotine or a nicotine derivative, the heating element heats the vaporizable material to about 250 degrees Celsius.

In one embodiment, the heating element is housed within a vaporization chamber surrounded by vaporization chamber walls. The vaporization chamber is also referred to as the atomizer. In some embodiments, the vaporization chamber walls can be constructed of any material capable of withstanding repeated heating to the operating temperature of the vaporizer device. In some embodiments, the vaporization chamber walls can be constructed of any material capable of withstanding repeated heating to 300 degrees Celsius. The vaporization chamber possesses an air inlet, to allow the entrance of air to the atomizer, and an air outlet, to allow vapor to escape to the user. Vaporizable material is introduced to the atomizer by a wick, which is in fluid communication with a vaporizable material. The vaporizable material can be stored in a tank integral to the electronic vaporizer device or in a removable tank (pod), configured to be detached from the vaporizer device after it is depleted. In an alternative embodiment, the heater element is in an oven configuration, wherein the heating element surrounds a chamber with stainless steel walls, and heats a vaporizable material, placed within the chamber, by conduction. In an oven configuration, the inside of the oven can be exposed to the outside by removal of an oven lid, which allows loading of a vaporizable material. The oven can further contain an outlet that allows vapor to escape to the user.

In any of the vaporizer devices described herein, the apparatus may include a heater controller (e.g., a heating element controller). In certain embodiments, the heater controller operates the heating element. In certain embodiments, the heater controller switches the heater on and off, and/or switches the heater on and off in a rapid "pulsed" fashion. In certain embodiments, the heater controller is configured to detect and/or control the power delivered from the power source. In certain embodiments, the heater controller is configured to detect and/or control the voltage delivered from the power source. In certain embodiments, the heater controller is configured to detect and/or control the current delivered from the power source. In certain embodiments, the heater controller is configured to detect and/or control the power, voltage and/or current delivered, or any combination thereof from the power source. In certain embodiments, the heater controller is connected in series with the power source and the heater. In certain embodiments, the heater controller is connected to the power source in parallel with the heater. In certain embodiments, the heater controller is configured to detect and/or control the power delivered from the power source in Watts. In certain embodiments, the heater controller is configured to detect and/or control the voltage delivered from the power source in Volts. In certain embodiments, the heater controller is configured to detect and/or control the current delivered from the power source in Amps. In certain embodiments, the heater controller is communicatively coupled to the VMP unit.

In certain embodiments, the heater controller is configured to regulate the operation of the heater. In certain embodiments, the heater controller is configured to regulate the temperature of the heater. In certain embodiments, the heater controller is configured to regulate the voltage delivered to the heater by the power source. In certain embodiments, the heater controller is configured to regulate the current delivered to the heating element by the power source. In certain embodiments, the heater controller is configured to regulate the wattage delivered to the heater by the power source. In certain embodiments, the heater controller is configured to regulate the temperature of the heater by regulating power delivered from the power source. In certain elements, the heating element controller is communicatively coupled to the processor. In certain embodiments, the heater controller is configured to receive instructions from the processor.

As discussed above, and described in U.S. patent application Ser. No. 14/581,666, the heater controller may use control logic (e.g., a PID loop) including one or more inputs such as the temperature, e.g., determined using the coefficient of resistance or TCR of the heater. Thus, in determining the dose (e.g., partial doses of a puff), the apparatus may advantageously use just electrical values (resistance and power values) from the controller, once calibrated with the appropriate constants (which may be analytically or theoretically determined as mentioned above, or may be assumed/ignored).

Cartridge

As described above, in some embodiments, the electronic vaporizer device utilizing the method of determining the amount of vapor delivered to the user described herein, such as device 100, includes a separate detachable pod configured to hold a vaporizable material. In certain embodiments, the pod is any receptacle or tank configured to hold a vaporizable material. In certain embodiments, the pod is removable. In certain embodiments, the pod is replaceable. In certain embodiments, the pod and the electronic vaporizer device form a single unit after the pod is attached to the electronic vaporizer device. In certain embodiments, the pod further comprises a mouthpiece. In certain embodiments, the electronic vaporizer device utilizing the method does not comprise a separate pod configured to hold a vaporizable material, and vaporizable material is stored in the electronic vaporizer device. In certain embodiments, the separate pod contains a vaporization chamber. In certain embodiments, the pod holds between. 1 and 10 ml of a liquid, viscous liquid or wax. In certain embodiments, the pod holds between 1 and 10 ml of a liquid, viscous liquid or wax. In certain embodiments, the pod holds between. 1 and 2 ml of a liquid, viscous liquid or wax. In certain embodiments, the pod holds between. 5 and 1.5 ml of a liquid, viscous liquid or wax.

In some embodiments, the cartridge can be filled with non-hydroscopic solvents and/or be substantially airtight so as to avoid absorption of water in the cartridge, thereby ensuring a predictable and accurate dose calculation.

Temperature Sensor

As described above, any of the vaporizer apparatuses described herein, such as devices 10, 100, 100' in FIGS. 1A-1C, can include one or more temperature sensors, such as temperature sensor 250. In certain embodiments, the temperature sensor is configured to measure the temperature of the heating element. The temperature sensor may include software and hardware for measuring the resistance that may be integral with (or separate from) any of the controller and/or processors described herein. In certain embodiments, the temperature sensor is configured to measure the temperature of a vaporization chamber housing the heating element. In certain embodiments, the temperature sensor is configured to measure the temperature of an oven chamber heated by the heating element. In certain embodiments, the temperature sensor measures heat in degrees Celsius. In certain embodiments, the temperature sensor measures heat in degrees Fahrenheit. In certain embodiments, the temperature sensor measures heat in degrees Kelvin. In certain embodiments, the temperature sensor is a thermocouple. In certain embodiments, the temperature sensor is a thermistor. In certain embodiments, the temperature sensor is an infrared temperature sensor. In certain embodiments, the temperature sensor is a relative resistance gradient measurement system. In certain embodiments, the temperature sensor is the heater coil used to heat the vaporizable material.

In certain embodiments, the temperature sensor measures a temperature to an accuracy of ±0.1 degrees Celsius. In certain embodiments, the temperature sensor measures a temperature to an accuracy of ±0.2 degrees Celsius. In certain embodiments, the temperature sensor measures a temperature to an accuracy of ±0.3 degrees Celsius. In certain embodiments, the temperature sensor measures a temperature to an accuracy of ±0.4 degrees Celsius. In certain embodiments, the temperature sensor measures a temperature to an accuracy of 0.5 degrees Celsius. It should be noted that the accuracy of the measured temperature may be as poor as +/−25° C. (e.g., less than 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., etc.). In certain embodiments, the temperature sensor measures temperature indirectly by measuring the resistance of the heating element. In certain embodiments, resistance is measured in Ohms. In certain, embodiments, the temperature sensor is capable of measuring a temperature profile, which is a change in temperature over time.

Puff Sensor

As described above, the vaporizer apparatuses described herein may optionally include a puff sensor. In certain embodiments, the puff sensor measures the initiation of the users puff. In certain embodiments, the puff sensor measures the cessation of the users puff. In certain embodiments, the puff sensor measures the duration of the users puff. In certain embodiments, the puff sensor measures the velocity and amount of air traveling through the electronic vaporizer device. In certain embodiments, the puff sensor is a button that is pressed upon initiation of a user's puff. In certain embodiments, the puff sensor is a pressure sensor. In certain embodiments, the pressure sensor is a Venturi meter. In certain embodiments, the pressure sensor is an orifice plate. In certain embodiments, the pressure sensor is a Dall tube. In certain embodiments, the pressure sensor is a pitot-static tube. In certain embodiments, the pressure sensor is a multi-hole pressure probe. In certain embodiments, the pressure sensor is a cone meter. In certain embodiments, the puff sensor comprises a button that is pressed by the user to initiate a puff. In certain embodiments, the puff sensor is a flow meter. In certain embodiments, the flow meter is a turbine flow meter. In certain embodiments, the puff sensor is communicatively coupled to the VMP unit. In certain embodiments, the puff sensor is configured to measure a puff initiated by the user. In certain embodiments, the puff sensor is configured to measure a puff initiated by an analytical smoking machine.

Timer

In certain embodiments, the electronic vaporizer device utilizing the method of determining the amount of vapor delivered to the user described herein, such as device 100, includes a timer. In a certain embodiment, the timer is communicatively coupled to the temperature sensor. In certain embodiments, the timer is communicatively coupled to the puff sensor. In certain embodiments, the timer measures a puff duration. In certain embodiments, the timer measures a puff frequency. In certain embodiments, the timer is communicatively coupled to the VMP unit. In certain embodiments, the timer is communicatively coupled to both the puff sensor and the VMP unit. In some instances, a puff duration can range from about 0.1 seconds to about 10 seconds. In some instances, a puff duration can range from about 1 second to about 5 seconds. In some instances, a puff duration can range from about 1 second to about 4 seconds. In some instances, a puff duration can range from about 1 second to about 3 seconds. In some instances, a puff duration can range from about 1 second to about 2 seconds. In certain embodiments, the accuracy of a measurement of the puff duration is within about ±0.05 seconds. In certain embodiments, the accuracy of a measurement of the puff duration is within about ±0.1 seconds. In certain embodiments, the accuracy of a measurement of the puff duration is within about +0.2 seconds. In certain embodiments, the accuracy of a measurement of the puff duration is within about ±0.3 seconds. In certain embodiments, the accuracy of a measurement of the puff duration is within about ±0.4 seconds. In certain embodiments, the accuracy of a measurement of the puff duration is within about +0.5 seconds.

Figure 7:
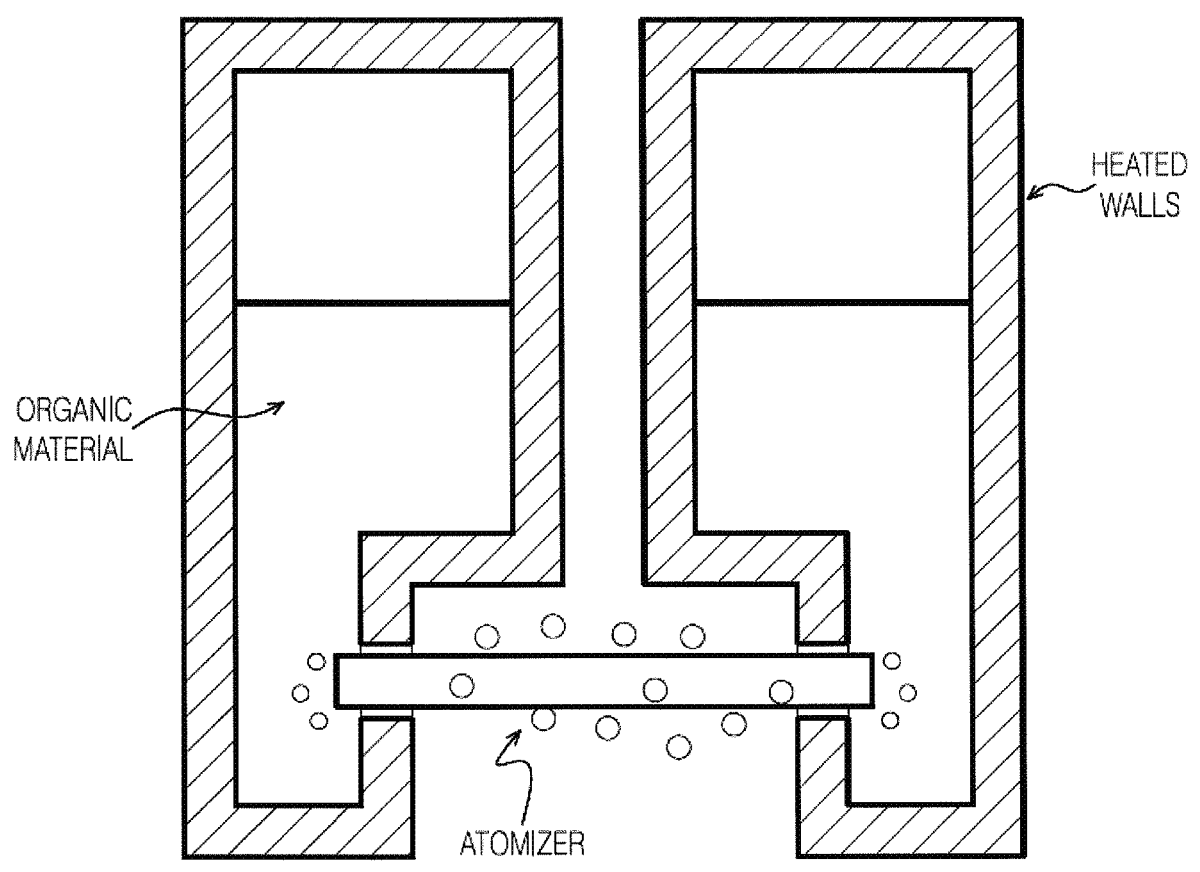

In some variations, the heated reservoir may be heated. Referring to FIG. 7, in certain embodiments, the electronic vaporizer device utilizing the method of determining the amount of vapor delivered to the user described herein, such as device 100, includes a heat block reservoir (or heat reservoir or heat block).

Figure 8:
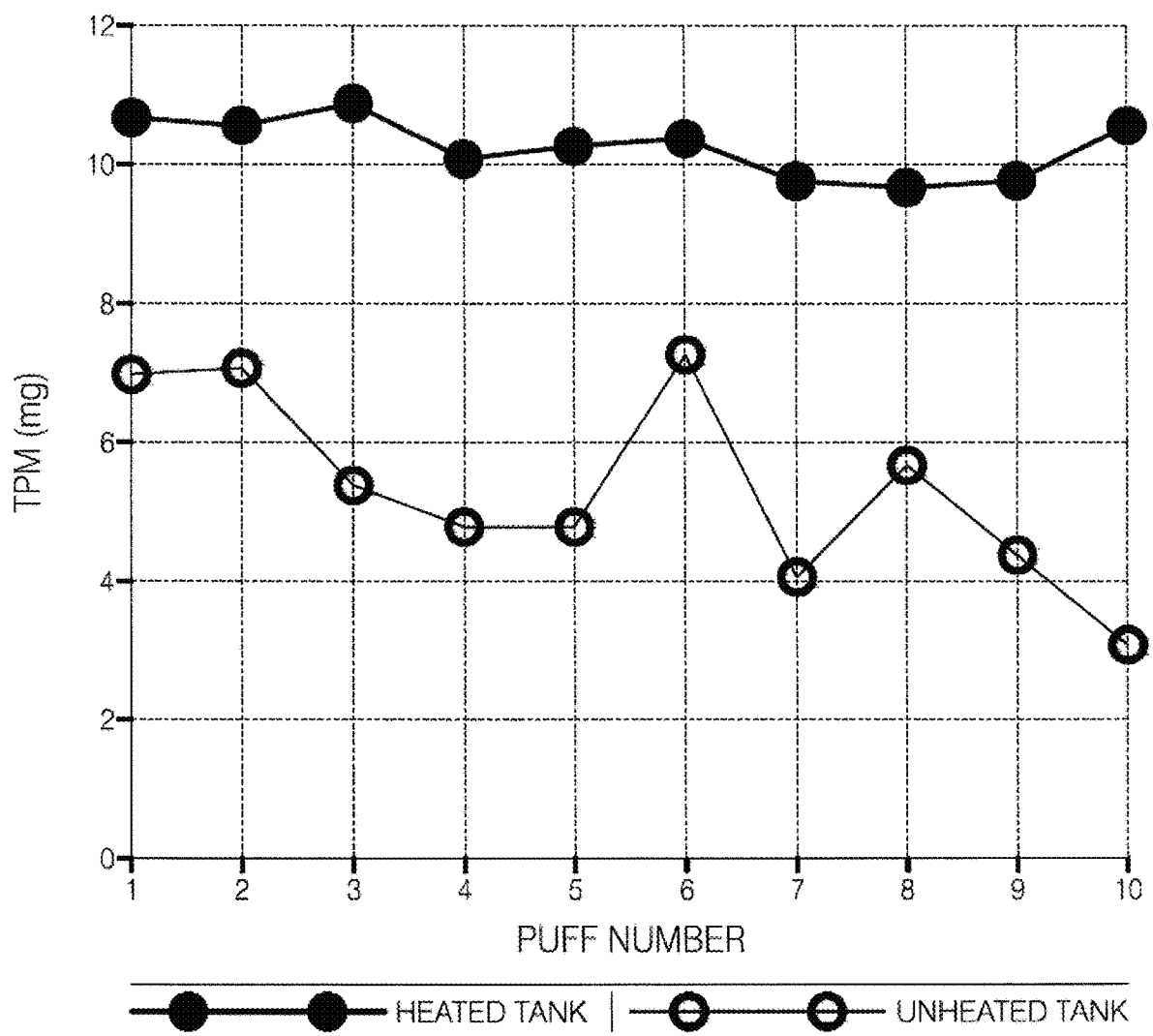
FIG. 8 is a graph illustrating the number of puffs relative to the TPM release content (mg) of a non-heated reservoir of an electronic vaporizer device compared with the number of puffs relative to the TPM release content (mg) of a heat reservoir of an electronic vaporizer device having a heated reservoir ("tank").

Heating the reservoir may allow for a more controlled initial state, which may enhance the predictability of the dose estimation. This is illustrated in FIG. 8. In some variations, and particularly those illustrated above, heating the reservoir may be unnecessary as sufficiently accurate dose (vapor) estimations may be determined. FIGS. 9A and 9B conceptual relate to a model which may benefit from using a heated reservoir. Alternatively, just the portion of the vaporizable material feeding into the vaporizing region (e.g., wick) may be heated.

Smoking vaporizable organic formulations that may be thick (non-flowing) or non-liquid with electronic vaporizer devices can pose a challenge. However, there remains an unmet need of vaporizing organic formulations that are otherwise thick (non-flowing) liquids or non-liquids, that include, but are not limited to, for example, *Cannabis* extracts. In certain embodiments, the heat reservoir is distinct form the heating element. In certain embodiments, the heat reservoir is fluidly coupled to the heater element. In certain embodiments, the heat reservoir is constructed of stainless steel. In certain embodiments, the heat reservoir is constructed of high temperature plastic. In certain embodiments, the heat reservoir preheats a viscous, semi-solid or solid composition, before vaporization with the heating element. In certain embodiments, the heat reservoir preheats a vaporizable material to between 40 degrees Celsius and 100 degrees Celsius. In certain embodiments, the heat reservoir preheats a vaporizable material to between 40 degrees Celsius and 80 degrees Celsius. In certain embodiments, the heat reservoir preheats a vaporizable material to between 40 degrees Celsius and 60 degrees Celsius. In certain embodiments, the heat reservoir preheats a vaporizable material to about 50 degrees Celsius. In certain embodiments, the heat reservoir preheats a vaporizable material to between 50 degrees Celsius and 100 degrees Celsius. In certain embodiments, the heat reservoir preheats a vaporizable material to between 60 degrees Celsius and 100 degrees Celsius. In certain embodiments, the heat reservoir preheats a vaporizable material to between 70 degrees Celsius and 100 degrees Celsius. In certain embodiments, the heat reservoir preheats a vaporizable material to between 80 degrees Celsius and 100 degrees Celsius. In certain embodiments, the heat reservoir preheats a vaporizable material to between 90 degrees Celsius and 100 degrees Celsius. In certain embodiments, the heat block is configured to warm material that exhibits a viscosity between 50 and 1000 Centipoise. In certain embodiments, the heat block is configured to warm material that exhibits a viscosity between 1,000 and 5,000 Centipoise. In certain embodiments, the heat block is configured to warm material that exhibits a viscosity between 5,000 and 50,000 Centipoise. In certain embodiments, the heat block is configured to warm material that exhibits a viscosity above 5,000 Centipoise (or above 10,000 Centipoise, above 20,000 Centipoise, above 30,000 Centipoise, above 40,000 Centipoise, etc.).

An analytical vaporizer device smoking machine was employed in this example, which is similar to machines known in the art. An electronic vaporizer device including a heat block reservoir for thick (non-flowing) liquids or non-liquids, was compared to an electronic vaporizer device without a heat reservoir. The heat reservoir preheats the thick (non-flowing) liquids or non-liquids. When the thick (non-flowing) liquids or non-liquids are preheated prior to vaporization the effect of uneven heating is reduced during vaporization. FIG. 8 shows graphical data depicting the number of puffs relative to the TPM release content (mg) of a non-heated reservoir of an electronic vaporizer device compared with the number of puffs relative to the TPM release content (mg) of a heat reservoir of an electronic vaporizer device, where the latter's reservoir was pre-heated to a temperature of 40-60° C. Where the reservoir was pre-heated to a temperature of 40-60° C., a more or less consistent amount of TPM (mg) was generated from a viscous or thick non-flowing organic formulation; while the electronic vaporizer device without a heat block reservoir, vaporized inconsistent amounts of TPM (mg). An inconsistency of the TPM produced by the unheated reservoir can be a result of uneven heating of the vaporizable material.

Vaporizable Material

As described above, the vaporizer apparatuses described herein may be used with (and may include or be configured specifically for) any appropriate vaporizable material. In certain embodiments, the vaporizable material is an organic material. In certain embodiments, vaporizable material is a liquid, viscous liquid, wax or loose-leaf material. In certain embodiments, the vaporizable material is a tobacco-based material. In certain embodiments, the vaporizable material is a *Cannabis* based material. In certain embodiments, the vaporizable material is a botanical. In certain embodiments, the vaporizable material is nicotine, a nicotine derivative or a nicotine salt. In certain embodiments, the vaporizable material is a nutraceutical. In certain embodiments, the vaporizable material contains a cannabinoid. In certain embodiments, the vaporizable material is a medicinal compound.

In certain embodiments, the vaporizable material exhibits a viscosity between 1 and 50 Centipoise. In certain embodiments, the vaporizable material exhibits a viscosity between 50 and 1,000 Centipoise. In certain embodiments, the vaporizable material exhibits a viscosity between 1,000 and 5,000 Centipoise. In certain embodiments, the vaporizable material exhibits a viscosity between 5,000 and 10,000 Centipoise. In certain embodiments, the vaporizable material exhibits a viscosity above 10,000 Centipoise.

In certain embodiments, the vaporizable material contains nicotine. In certain embodiments, the vaporizable material contains a nicotine derivative. In certain embodiments, the nicotine derivative is an acid salt of nicotine. In certain embodiments, the acid salt of nicotine comprises an organic acid. In certain embodiments, the acid salt of nicotine does not comprise an inorganic acid. In certain embodiments, the nicotine derivative is cotinine. In certain embodiments, the nicotine derivative is norcotinine. In certain embodiments, the nicotine derivative is nornicotine. In certain embodiments, the nicotine derivative is nicotine N-oxide. In certain embodiments, the nicotine derivative is cotinine N-oxide. In certain embodiments, the nicotine derivative is 3-hydroxycotinine. In certain embodiments, the nicotine derivative is 5-hydroxycotinine.

In certain embodiments, the vaporizable material is a formulation of nicotine, nicotine derivatives, or a nicotine salt. In some formulations the concentration of nicotine or derivatives thereof in the formulation is about 1% (w/w) to about 25% (w/w). In some formulations the concentration of nicotine or derivatives thereof; in the formulation is about 1% (w/w) to about 20% (w/w). In some formulations the concentration of nicotine in the formulation is about 1% (w/w) to about 18% (w/w). In some embodiments, the concentration of nicotine in the formulation is about 1% (w/w) to about 15% (w/w). In some embodiments, the concentration of nicotine in the formulation is about 1% (w/w) to about 10% (w/w). In some embodiments, the concentration of nicotine in the formulation is about 1% (w/w) to about 8% (w/w). In some embodiments, the concentration of nicotine in the formulation is about 2% (w/w) to about 10% (w/w). In some formulations the concentration of nicotine in the formulation is about 4% (w/w) to about 12% (w/w). In some formulations the concentration of nicotine in the formulation is about 4% (w/w). In some embodiments, the concentration of nicotine in the formulation is about 2% (w/w).

Nicotine salt formulations are formed by the addition of a suitable acid to nicotine or a derivative thereof, including organic or inorganic acids. In some formulations provided herein, suitable organic acids are carboxylic acids. Examples of organic carboxylic acids disclosed herein are monocarboxylic acids, dicarboxylic acids (organic acid containing two carboxylic acid groups), carboxylic acids containing an aromatic group such as benzoic acids, hydroxycarboxylic acids, heterocyclic carboxylic acids, terpenoid acids, sugar acids; such as the pectic acids, amino acids, cycloaliphatic acids, aliphatic carboxylic acids, keto carboxylic acids, and the like. In some formulations provided herein, the organic acids used herein are monocarboxylic acids. In some formulations provided herein the organic carboxylic acid is benzoic, levulinic, acetic, lactic, citric, sorbic, lauric, salicylic, pyruvic or a combination thereof. In some formulations provided herein the organic carboxylic acid is not levulinic. Nicotine salts are formed from the addition of a suitable acid to nicotine. In some formulations provided herein, the stoichiometric ratios of the nicotine to acid (nicotine:acid) are 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In some formulations provided herein, the stoichiometric ratios of the nicotine to acid are 1:1, 1:2, 1:3, or 1:4 (nicotine:acid).

In certain embodiments, the pH of the nicotine formulation is acidic. In certain embodiments, the pH of the nicotine formulation is <7.0. In certain embodiments, the pH of the nicotine formulation is <6.0. In certain embodiments, the pH of the nicotine formulation is <5.0. In certain embodiments, the pH of the nicotine formulation is <4.0. In certain embodiments, the pH of the nicotine formulation is >3.0. In certain embodiments, the pH of the nicotine formulation is >4.0. In certain embodiments, the pH of the nicotine formulation is >5.0. In certain embodiments, the pH of the nicotine formulation is >6.0.

In certain embodiments, the vaporizable material contains organic material from a *Cannabis* genus plant. In certain embodiments, the vaporizable material contains an extract from a *Cannabis* genus plant. In certain embodiments, the vaporizable material contains a cannabinoid. In certain embodiments, the cannabinoid is tetrahydrocannabinol (THC). In certain embodiments, the cannabinoid is carmabigerolic acid (CBGA). In certain embodiments, the cannabinoid is cannabigerol (CBG). In certain embodiments, the cannabinoid is tetrahydrocannabinolic acid (THCA). In certain embodiments, the cannabinoid is cannabichromene (CBC). In certain embodiments, the cannabinoid is cannabicyclol (CBL). In certain embodiments, the cannabinoid is cannabivarin (CBV). In certain embodiments, the cannabinoid is cannabichromevarin (CBCV). In certain embodiments, the cannabinoid is cannabigerovarin (CBGV). In certain embodiments, the cannabinoid is cannabigerol Monomethyl Ether (CBGM). In certain embodiments, the cannabinoid is delta-8-tetrahydrocannabinol (D8THC). In certain embodiments, the cannabinoid is delta-9-tetrahydrocannabinol (D9THC). In certain embodiments, the cannabinoid is tetrahydrocannabivarin (THCV). In certain embodiments, the cannabinoid is cannabinolic acid (CBNA). In certain embodiments, the cannabinoid is Cannabinol (CBN). In certain embodiments, the cannabinoid is cannabidiolic acid (CBDA). In certain embodiments, the cannabinoid is Cannabidivaric acid (CBDVA). In certain embodiments, the cannabinoid is cannabidiol (CBD). In certain embodiments, the cannabinoid is cannabichromenic acid (CBCA). In certain embodiments, the cannabinoid is Cannabichromene (CBC). In certain embodiments, the cannabinoid is cannabicyclolic acid (CBLA). In certain embodiments, the cannabinoid is an stereo isomer of any of the above mentioned cannabinoids. In certain embodiments, the cannabinoid is a salt of any of the above mentioned cannabinoids.

In certain embodiments, the vaporizable material is a cannabinoid formulation. In certain embodiments, the concentration of cannabinoid in the cannabinoid formulation is from 1-99% cannabinoid. In certain embodiments, the concentration of cannabinoid in the cannabinoid formulation is from 5-95% cannabinoid. In certain embodiments, the concentration of cannabinoid in the cannabinoid formulation is from 10-90% cannabinoid. In certain embodiments, the concentration of cannabinoid in the cannabinoid formulation exceeds about 99% cannabinoid. In certain embodiments, the concentration of cannabinoid in the cannabinoid formulation exceeds about 98% cannabinoid. In certain embodiments, the concentration of cannabinoid in the cannabinoid formulation exceeds about 97% cannabinoid. In certain embodiments, the concentration of cannabinoid in the cannabinoid formulation exceeds about 96% cannabinoid. In certain embodiments, the concentration of cannabinoid in the cannabinoid formulation exceeds about 95% cannabinoid. In certain embodiments, the concentration of cannabinoid in the cannabinoid formulation exceeds about 94% cannabinoid. In certain embodiments, the concentration of cannabinoid in the cannabinoid formulation exceeds about 93% cannabinoid. In certain embodiments, the concentration of cannabinoid in the cannabinoid formulation exceeds about 92% cannabinoid. In certain embodiments, the concentration of cannabinoid in the cannabinoid formulation exceeds about 91% cannabinoid. In certain embodiments, the concentration of cannabinoid in the cannabinoid formulation exceeds about 90% cannabinoid. In certain embodiments, the concentration of cannabinoid in the cannabinoid formulation exceeds about 80% cannabinoid. In certain embodiments, the concentration of cannabinoid in the cannabinoid formulation exceeds about 70% cannabinoid. In certain embodiments, the concentration of cannabinoid in the cannabinoid formulation exceeds about 60% cannabinoid. In certain embodiments, the concentration of in the cannabinoid formulation exceeds about 50% cannabinoid. In certain embodiments, the concentration of in the cannabinoid formulation exceeds about 40% cannabinoid. In certain embodiments, the concentration of cannabinoid in the cannabinoid formulation exceeds about 30% cannabinoid. In certain embodiments, the concentration of cannabinoid in the cannabinoid formulation exceeds about 20% cannabinoid. In certain embodiments, the concentration of cannabinoid in the cannabinoid formulation exceeds about 10% cannabinoid. In certain embodiments, the concentration of cannabinoid in the cannabinoid formulation is from about 1% to about 10% cannabinoid. In certain embodiments, the concentration of cannabinoid in the cannabinoid formulation is from about 10% to about 20% cannabinoid. In certain embodiments, the concentration of cannabinoid in the cannabinoid formulation is from about 20% to about 30% cannabinoid. In certain embodiments, the concentration of cannabinoid in the cannabinoid formulation is from about 30% to about 40% cannabinoid. In certain embodiments, the concentration of cannabinoid in the cannabinoid formulation is from about 40% to about 50% cannabinoid. In certain embodiments, the concentration of cannabinoid in the cannabinoid formulation is from about 50% to about 60% cannabinoid. In certain embodiments, the concentration of cannabinoid in the cannabinoid formulation is from about 60% to about 70% cannabinoid. In certain embodiments, the concentration of cannabinoid in the cannabinoid formulation is from about 70% to about 80% cannabinoid. In certain embodiments, the concentration of cannabinoid in the cannabinoid formulation is from about 80% to about 90% cannabinoid. In certain embodiments, the concentration of cannabinoid in the cannabinoid formulation is from about 90% to about 100% cannabinoid.

In certain embodiments, the pH of the cannabinoid formulation is acidic. In certain embodiments, the pH of the cannabinoid formulation is <7.0. In certain embodiments, the pH of the cannabinoid formulation is <6.0 In certain embodiments, the pH of the cannabinoid formulation is <5.0. In certain embodiments, the pH of the cannabinoid formulation is <4.0. In certain embodiments, the pH of the cannabinoid formulation is >3.0. In certain embodiments, the pH of the cannabinoid formulation is >4.0. In certain embodiments, the pH of the cannabinoid formulation is >5.0. In certain embodiments, the pH of the cannabinoid formulation is >6.0. In certain embodiments, the pH of the cannabinoid formulation is basic. In certain embodiments, the pH of the cannabinoid formulation is <10.0. In certain embodiments, the pH of the cannabinoid formulation is <9.0 In certain embodiments, the pH of the cannabinoid formulation is <8.0. In certain embodiments, the pH of the cannabinoid formulation is >7.0. In certain embodiments, the pH of the cannabinoid formulation is >8.0. In certain embodiments, the pH of the cannabinoid formulation is >9.0. In certain embodiments, the pH of the cannabinoid formulation is >10.0.

In certain embodiments, the vaporizable material is a *Cannabis* formulation. In certain embodiments, the concentration of the *Cannabis* formulation is from 1-99% *Cannabis*. In certain embodiments, the concentration of the *Cannabis* formulation is from 5-95% *Cannabis*. In certain embodiments, the concentration of the *Cannabis* formulation is from 10-90% *Cannabis*. In certain embodiments, the *Cannabis* formulation exceeds about 99% *Cannabis*. In certain embodiments, the *Cannabis* formulation exceeds about 98% *Cannabis*. In certain embodiments, the *Cannabis* formulation exceeds about 97% *Cannabis*. In certain embodiments, the *Cannabis* formulation exceeds about 96% *Cannabis*. In certain embodiments, the *Cannabis* formulation exceeds about 95% *Cannabis*. In certain embodiments, the *Cannabis* formulation exceeds about 94% *Cannabis*. In certain embodiments, the *Cannabis* formulation exceeds about 93% *Cannabis*. In certain embodiments, the *Cannabis* formulation exceeds about 92% *Cannabis*. In certain embodiments, the *Cannabis* formulation exceeds about 91% *Cannabis*. In certain embodiments, the *Cannabis* formulation exceeds about 90% *Cannabis*. In certain embodiments, the *Cannabis* formulation exceeds about 80% *Cannabis*. In certain embodiments, the *Cannabis* formulation exceeds about 70% *Cannabis*. In certain embodiments, the *Cannabis* formulation exceeds about 60% *Cannabis*. In certain embodiments, the *Cannabis* formulation exceeds about 50% *Cannabis*. In certain embodiments, the *Cannabis* formulation exceeds about 40% *Cannabis*. In certain embodiments, the *Cannabis* formulation exceeds about 30% *Cannabis*. In certain embodiments, the *Cannabis* formulation exceeds about 20% *Cannabis*. In certain embodiments, the *Cannabis* formulation exceeds about 10% *Cannabis*.

In certain embodiments, the pH of the *Cannabis* formulation is acidic. In certain embodiments, the pH of the *Cannabis* formulation is <7.0. In certain embodiments, the pH of the *Cannabis* formulation is <6.0 In certain embodiments, the pH of the *Cannabis* formulation is <5.0. In certain embodiments, the pH of the *Cannabis* formulation is <4.0. In certain embodiments, the pH of the *Cannabis* formulation is >3.0. In certain embodiments, the pH of the *Cannabis* formulation is >4.0. In certain embodiments, the pH of the *Cannabis* formulation is >5.0. In certain embodiments, the pH of the *Cannabis* formulation is >6.0. In certain embodiments, the pH of the *Cannabis* formulation is basic. In certain embodiments, the pH of the *Cannabis* formulation is <10.0. In certain embodiments, the pH of the *Cannabis* formulation is <9.0 In certain embodiments, the pH of the *Cannabis* formulation is <8.0. In certain embodiments, the pH of the *Cannabis* formulation is >7.0. In certain embodiments, the pH of the *Cannabis* formulation is >8.0. In certain embodiments, the pH of the *Cannabis* formulation is >9.0. In certain embodiments, the pH of the *Cannabis* formulation is >10.0.

In certain embodiments, the vaporizable material contains a medicinal compound as an active ingredient. The medicinal compounds that are active ingredients for vaporization with the electronic vaporizer device utilizing the method herein, include drugs that can be heated without combustion to vaporization for inhalation delivery at a temperature range of, e.g., about 100° C. (e.g., for water-based carriers, e.g., about 100° C., 105° C., 110° C., 120° C., 130° C., 140° C., 150° C., 160° C., 170° C., etc.; for ethanol-based formulations, e.g., about 50° C., about 60° C., about 70° C., about 80° C., etc.) to about (e.g., below) the temperature at which the active ingredient thermally decomposes (e.g., less than about 150° C., 160° C., 170° C., 180° C., 190° C., 200° C., 210° C., 220° C., 230° C., 240° C., 250° C., 260° C., 270° C., 280° C., 290° C., 300° C., etc.). In certain embodiments, the drugs can be neat or are solubilized in a pharmaceutically acceptable solvent. In certain embodiments, the drugs can include over the counter (OTC) substances as aides for various ailments; wherein said drugs can include known respiratory aides for asthma or chronic obstructive pulmonary disease (COPD). The vaporizable materials that are active ingredients for vaporization with the device(s) herein described, can include drugs that can be heated to vaporization for inhalation delivery, without combustion; wherein said drugs can include over the counter (OTC) substances from the group comprising upper respiratory aides (like cetirizine), analgesics and internal medication aides (like ibuprofen, naproxen), heartburn aides (like omeprazole), sleeping aides (like doxylamine, diphenhydramine, melatonin), or motion sickness aides (like meclizine). In certain embodiments, the vaporizable material can contain respiratory aides for asthma or chronic obstructive pulmonary disease (COPD) such as short acting beta-agonist (like albuterol, levalbuterol, pirbuterol), long acting beta-agonist (like salmeterol, formoterol), anti-cholinergics (like atropine sulfate, ipratropium bromide), leukotriene modifiers (like montelukast, zafirlukast), cartico-steriods (like fluticasone, budesonide, mometasone), theophylline (like theophylline), or combination corticosteroid and beta agonist, long lasting (fluticasone and salmeterol, budesonide and formoterol, mometasone and formoterol). In certain embodiments, the vaporizable material can contain botanicals and/or nutraceuticals such as tea (polyphenols, flavonoids, green tea catechins+/−caffeine); horehound (phenol flavonoid glycosides, labdane diterpenoids, yohimbe, cranberry/grape (proanthocyanidins), black cohosh (terpene glycoside fraction (actine/cimifugoside), flax seed (omega fatty acids), echinacea (echinacoside), valerian (alkaloids, gabapentin, isovaleric acid, terpenes), senna (senna cglycosides), cinnamon (cinnamaldehyde, phenols, terpenes), vitamin D, saw palmetto (fatty acids), or caffeine. In certain embodiments, the vaporizable material is soluble to at least fifty percent by weight in any suitable carrier solvent such as glycols (such as propylene glycol and vegetable glycerin), ethylene glycol, dipropylene glycol, trimethylene glycol, ethanol, and combinations thereof. In certain embodiments, the medicinal compound is terpinolene. In certain embodiments, the medicinal compound is Linalool. In certain embodiments, the medicinal compound is phytol, In certain embodiments, the medicinal compound is beta myrcene. In certain embodiments, the medicinal compound is citronellol. In certain embodiments, the medicinal compound is caryophyllene oxide. In certain embodiments, the medicinal compound is alpha pinene. In certain embodiments, the medicinal compound is limonene. In certain embodiments, the medicinal compound is beta caryophyllene. In certain embodiments, the medicinal compound is humulene. In certain embodiments, the vaporizable material is an essential oil.

User Interface

In certain embodiments, the vaporizer apparatuses described herein may include a user interface. In certain embodiments, the user interface is a display. In certain embodiments, the display is an LCD. In certain embodiments, the display is an LED. In certain embodiments, the display is an OLED. In certain embodiments, the display provides a user interface. In certain embodiments, the display is touch sensitive. In certain embodiments, the display communicates puff frequency, puff duration, amount of TPM vaporized, amount of active ingredient vaporized, or any combination thereof. In certain embodiments, the display allows the user to select the type of vaporizable material. In certain embodiments, the display allows the user to select the amount of vaporizable material vaporized before the alert unit alerts the user or the vaporizer device is disabled, or both. In certain embodiments, the electronic vaporizer device utilizing the method comprises a user interface controller. In certain embodiments, the user interface controller is communicatively coupled to the display. In certain embodiments, the user interface controller is a software module that controls information communicated via the display.

In some embodiments, the user interface can be configured to allow a user to change and/or monitor the settings and state of the electronic vaporizer device. For example, in one embodiment, user control means can be used to limit the usage of the device, relative to any of calculated TPM, puff duration, puff volume, voltage or heat temperature, singly or in combination.

Further, the vaporizer device described herein can include at least one of a switch, a keypad, a display, an input/output port, and a wireless transceiver. In one embodiment, the input/output port and the wireless transceiver can be employed to create a communications link between the control unit of the electronic vaporizer device and an external computer, such as a cell phone or personal computer.

The foregoing disclosure and description of the invention are illustrative and explanatory thereof and various adaptations may be made without departing from the spirit of the invention.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of estimating an amount of a substance delivered to a user of a vaporizer device over a dose interval, the method comprising:
    determining an amount of power applied to a heater of the vaporizer device, the heater configured to vaporize a vaporizable material;
    determining an initial temperature of the heater at a first time, the first time being at the start of the dose interval;
    determining a second temperature of the heater of the vaporizer device at a second time, the second time subsequent to the first time;
    determining, based on the amount of power applied to the heater and a difference between the initial temperature and the second temperature, the estimated amount of the substance delivered to the user of the vaporizer device;
    calculating, based on a first constant multiplied by the difference between the initial temperature and the second temperature, a first value;
    calculating, based on a second constant multiplied by the second temperature, a second value;
    calculating, based on the power applied to the heater subtracted by both the first and second values, a third value; and
    calculating, based on a third constant multiplied by the third value, the estimated amount of the substance delivered to the user of the vaporizer device.

2. The method of claim 1, wherein the vaporizer device comprises the vaporizable material.

3. The method of claim 1, wherein the vaporizable material comprises the substance.

4. The method of claim 1, wherein the substance comprises an amount of an active ingredient delivered to the user.

5. The method of claim 1, wherein the vaporizable material comprises nicotine and a carrier.

6. The method of claim 5, wherein the carrier comprises one or more glycols.

7. The method of claim 1, wherein the vaporizable material comprises a tobacco-based material.

8. The method of claim 1, wherein the vaporizable material comprises a botanical.

9. The method of claim 1, wherein the vaporizable material comprises a nicotine compound.

10. The method of claim 1, wherein the vaporizable material comprises a cannabinoid.

11. The method of claim 1, wherein the vaporizable material comprises at least one of: cetirizine, ibuprofen, naproxen, omeprazole, doxylamine, diphenhydramine, melatonin, or meclizine.

12. The method of claim 1, wherein the vaporizable material comprises at least one of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, and mometasone and formoterol.

13. The method of claim 1, wherein the vaporizable material comprises at least one of: a polyphenol, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, and Vitamin D.

14. The method of claim 1, wherein the vaporizable material comprises a nicotine salt, glycerin, and propylene glycol.

15. The method of claim 1, wherein the estimated amount of the substance delivered to the user comprises an estimate of the substance delivered during the dose interval.

16. The method of claim 1, further comprising:
    detecting a user's puff on the vaporizer device, wherein a time period corresponding to a duration of the detected user's puff comprises the dose interval.

17. The method of claim 1, further comprising:
    determining, for a time period comprising a plurality of partial dose intervals, a plurality of estimated partial doses delivered to the user based on: power applied to the heater before or at a start of each partial dose interval, a temperature of the heater at the start and at an end of each partial dose interval; and
    determining, based on a sum of the plurality of estimated partial doses, a total estimated dosage delivered to the user over the time period.

18. The method of claim 17, wherein determining the total estimated dosage delivered comprises aggregating the plurality of estimated partial doses as each of the plurality of estimated partial doses are calculated.

19. The method of claim 1, further comprising:
    disabling the vaporizer device when the estimated amount of the substance delivered, over a time period, meets or exceeds a preset threshold.

20. The method of claim 1, further comprising:
    alerting the user when the estimated amount of the substance delivered, over a time period, meets or exceeds a preset threshold.

21. The method of claim 1, wherein determining the initial temperature comprises calculating, based on an electrical property of the heater that is proportional to a temperature of the heater, an estimate of the initial temperature.

22. The method of claim 1, further comprising:
    transmitting, by the vaporizer device to a separate device for determining the estimated amount of the substance, one or more of the amount of power applied to the heater, the initial temperature, and the second temperature.

23. A vaporizer device comprising:
    a heater configured to vaporize a vaporizable material; and
    one or more controllers configured to perform operations comprising:
        determining an amount of power applied to the heater;
        determining an initial temperature of the heater at a first time, the first time being at the start of a dose interval;
        determining a second temperature of the heater at a second time, the second time subsequent to the first time;
        determining, based on the amount of power applied to the heater and a difference between the initial temperature and the second temperature, an estimated amount of a substance delivered to a user;
        determining, based on at least one of a latent heat of the vaporizable material, a specific heat of the vaporizable material, and a mass of the vaporizable material and the heater, a set of constants;

calculating, based on the set of constants, the initial temperature, the second temperature, and the power applied to the heater, the estimated amount of the substance delivered to the user of the vaporizer device; and calibrating the vaporizer device by updating one or more constants in the set of constants.

24. The vaporizer device of claim 23, wherein the vaporizer device comprises the vaporizable material.

25. The vaporizer device of claim 23, wherein the vaporizable material comprises the substance.

26. The vaporizer device of claim 23, wherein the substance comprises an amount of an active ingredient delivered to the user.

27. The vaporizer device of claim 23, wherein the vaporizable material comprises nicotine and a carrier.

28. The vaporizer device of claim 27, wherein the carrier comprises one or more glycols.

29. The vaporizer device of claim 23, wherein the vaporizable material comprises a tobacco-based material.

30. The vaporizer device of claim 23, wherein the vaporizable material comprises a botanical.

31. The vaporizer device of claim 23, wherein the vaporizable material comprises a nicotine compound.

32. The vaporizer device of claim 23, wherein the vaporizable material comprises a cannabinoid.

33. The vaporizer device of claim 23, wherein the vaporizable material comprises at least one of: cetirizine, ibuprofen, naproxen, omeprazole, doxylamine, diphenhydramine, melatonin, or meclizine.

34. The vaporizer device of claim 23, wherein the vaporizable material comprises at least one of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, and mometasone and formoterol.

35. The vaporizer device of claim 23, wherein the vaporizable material comprises at least one of: a polyphenol, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, and Vitamin D.

36. The vaporizer device of claim 23, wherein the vaporizable material comprises a nicotine salt, glycerin, and propylene glycol.

37. The vaporizer device of claim 23, wherein the estimated amount of the substance delivered to the user comprises an estimate of the substance delivered during the dose interval.

38. The vaporizer device of claim 23, wherein the operations further comprise:

detecting a user's puff on the vaporizer device, wherein a time period corresponding to a duration of the detected user's puff comprises the dose interval.

39. The vaporizer device of claim 23, wherein the operations further comprise:

determining, for a time period comprising a plurality of partial dose intervals, a plurality of estimated partial doses delivered to the user based on: power applied to the heater before or at a start of each partial dose interval, a temperature of the heater at the start and at an end of each partial dose interval; and determining, based on a sum of the plurality of estimated partial doses, a total estimated dosage delivered to the user over the time period.

40. The vaporizer device of claim 39, wherein determining the total estimated dosage delivered comprises aggregating the plurality of estimated partial doses as each of the plurality of estimated partial doses are calculated.

41. The vaporizer device of claim 23, wherein the operations further comprise:

disabling the vaporizer device when the estimated amount of the substance delivered, over a time period, meets or exceeds a preset threshold.

42. The vaporizer device of claim 23, wherein the operations further comprise:

alerting the user when the estimated amount of the substance delivered, over a time period, meets or exceeds a preset threshold.

43. The vaporizer device of claim 23, wherein determining the initial temperature comprises calculating, based on an electrical property of the heater that is proportional to a temperature of the heater, an estimate of the initial temperature.

44. The vaporizer device of claim 23, wherein the one or more controllers comprise one or more of operating logic and software instructions.

45. The vaporizer device of claim 23, wherein the one or more controllers comprise a heater controller.

46. A vaporizer device comprising:

a heater configured to vaporize a vaporizable material; and one or more controllers configured to perform operations comprising:

determining an amount of power applied to the heater;

determining an initial temperature of the heater at a first time, the first time being at the start of a dose interval;

determining a second temperature of the heater at a second time, the second time subsequent to the first time;

determining, based on the amount of power applied to the heater and a difference between the initial temperature and the second temperature, an estimated amount of a substance delivered to a user;

calculating, based on a first constant multiplied by the difference between the initial temperature and the second temperature, a first value;

calculating, based on a second constant multiplied by the second temperature, a second value;

calculating, based on the power applied to a heater subtracted by both the first and second values, a third value; and calculating, based on a third constant multiplied by the third value, the estimated amount of the substance delivered to the user of the vaporizer device.

* * * * *